(12) United States Patent
Kaneko et al.

(10) Patent No.: US 12,006,512 B2
(45) Date of Patent: Jun. 11, 2024

(54) METHOD FOR PRODUCING CD8alpha+beta+ CYTOTOXIC T CELLS

(71) Applicant: KYOTO UNIVERSITY, Kyoto (JP)

(72) Inventors: Shin Kaneko, Kyoto (JP); Yohei Kawai, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 516 days.

(21) Appl. No.: 16/479,575

(22) PCT Filed: Jan. 19, 2018

(86) PCT No.: PCT/JP2018/001667
§ 371 (c)(1),
(2) Date: Jul. 19, 2019

(87) PCT Pub. No.: WO2018/135646
PCT Pub. Date: Jul. 26, 2018

(65) Prior Publication Data
US 2019/0367877 A1 Dec. 5, 2019

(30) Foreign Application Priority Data
Jan. 20, 2017 (JP) .................. 2017-008995

(51) Int. Cl.
| | | |
|---|---|---|
| C12N 5/0783 | (2010.01) | |
| A61K 35/17 | (2015.01) | |
| C12N 5/00 | (2006.01) | |
| C12N 5/074 | (2010.01) | |

(52) U.S. Cl.
CPC ............ *C12N 5/0638* (2013.01); *A61K 35/17* (2013.01); *C12N 5/0018* (2013.01); *C12N 5/0696* (2013.01); *C12N 2500/38* (2013.01); *C12N 2501/2307* (2013.01); *C12N 2501/2312* (2013.01); *C12N 2501/2315* (2013.01); *C12N 2501/2318* (2013.01); *C12N 2501/2321* (2013.01); *C12N 2501/26* (2013.01); *C12N 2501/42* (2013.01); *C12N 2501/50* (2013.01); *C12N 2501/998* (2013.01); *C12N 2506/45* (2013.01); *C12N 2533/52* (2013.01)

(58) Field of Classification Search
None
See application file for complete search history.

(56) References Cited

U.S. PATENT DOCUMENTS

| | | | |
|---|---|---|---|
| 10,660,915 B2 * | 5/2020 | Kaneko ................. | C12N 5/0636 |
| 2006/0269973 A1 | 11/2006 | Yee et al. | |
| 2009/0221077 A1 | 9/2009 | Ideno et al. | |
| 2011/0070185 A1 | 3/2011 | Cai et al. | |
| 2011/0236362 A1 * | 9/2011 | Watarai ................... | A61P 31/04 |
| | | | 435/375 |
| 2012/0142109 A1 * | 6/2012 | Katayama ............ | C12N 5/0636 |
| | | | 435/325 |
| 2013/0078226 A1 | 3/2013 | Nakauchi et al. | |
| 2013/0330360 A1 | 12/2013 | Andersen et al. | |
| 2014/0212398 A1 | 7/2014 | Reisner | |
| 2016/0194375 A1 * | 7/2016 | Kitchen ............. | C07K 14/7051 |
| | | | 435/325 |
| 2017/0326175 A1 | 11/2017 | Kaneko | |
| 2018/0333434 A1 * | 11/2018 | Bonini ................... | A61K 35/17 |
| 2018/0362927 A1 * | 12/2018 | Blazar .................. | C12N 5/0636 |
| 2019/0161727 A1 | 5/2019 | Kawamoto et al. | |
| 2019/0300591 A1 * | 10/2019 | Wong ..................... | C12N 15/81 |

FOREIGN PATENT DOCUMENTS

| | | |
|---|---|---|
| EP | 2853590 A1 | 4/2015 |
| JP | 2008-521406 A | 6/2008 |
| JP | 2014-509325 A | 4/2014 |
| JP | 2014-526244 A | 10/2014 |
| WO | WO 2005/019450 A1 | 3/2005 |
| WO | WO 2011/096482 A1 | 8/2011 |
| WO | WO 2013/035099 A1 | 3/2013 |
| WO | WO 2013/176197 A1 | 11/2013 |
| WO | WO 2016/076415 A1 | 5/2016 |
| WO | WO 2016/183350 A1 | 11/2016 |
| WO | WO 2016/191587 A1 | 12/2016 |
| WO | WO 2017/179720 A1 | 10/2017 |
| WO | WO 2017/221850 A1 | 12/2017 |
| WO | WO 2018/005712 A1 | 1/2018 |

OTHER PUBLICATIONS

Chen et al ( Shi, yan sheng wu xue bao, 1996, v.29, n. 1 p. 1).*
Extended European Search Report dated Aug. 12, 2020 in European Application No. 18741888.4.
Huijskens et al., Technical Advance: Ascorbic Acid Induces Development Of Double-Positive T Cells From Human Hematopoietic Stem Cells In The Absence Of Stromal Cells, Journal Of Leukocyte Biology, vol. 96, pp. 1165-1175, 2014.
Kawamoto et al., Cloning And Expansion Of Antigen-Specific T Cell Using Ips Cell Technology: Development Of "Off-The-Shelf" T Cells For The Use In Allogeneic Transfusion Settings, International Journal Of Hematology, vol. 107, pp. 271-277, 2018.
Kashima et al., Cytotoxic T Lymphocytes Regenerated from iPS Cells Have Therapeutic Efficacy in a Patient-Derived Xenograft Solid Tumor Model, iScience 23, 100998, 2020.
Kato et al., Inducing Effector T Cells, Proceedings Annual Meeting of the Japanese Cancer Association, 2008, in 1 page.

(Continued)

*Primary Examiner* — Michail A Belyavskyi
(74) *Attorney, Agent, or Firm* — Knobbe, Martens, Olson & Bear, LLP

(57) ABSTRACT

A method efficiently produces cytotoxic T lymphocytes having intrinsic properties of lymphocytes of the acquired immune system suitable for cellular immunotherapy. The method includes culturing CD4/CD8 double-positive T cells in a medium containing IL-7 and a T-cell receptor activator, to induce $CD8\alpha^+\beta^+$ cytotoxic T lymphocytes.

15 Claims, 16 Drawing Sheets

(56) References Cited

OTHER PUBLICATIONS

Maeda, T., et al., Regeneration of CD8αβ T Cells from T-Cell-Derived iPSC imparts Potent Tumor Antigen-Specific Cytotoxicity, Cancer Res, vol. 76, No. 23, pp. 6839-6850, 2016.
Nishimura et al., Generation of Rejuvenated Antigen-Specific T Cells by Reprogramming to Pluripotency and Redifferentiation, Cell Stem Cell, vol. 12, pp. 114-126, 2013.
Proceedings of the Japanese Society for Immunology, 2005, in 1 page.
Yoshiaki et al., Involvement of Notch Signaling in Differentiation into Cytotoxic T-Lymphocytes, Proceedings of the Japanese Society for Immunology, 2005, in 1 page.
Zoon, C.K., et al., Addition of Interleukin-21 for Expansion of T-cells for adoptive Immunotherapy of Murine Melanoma, International Journal of Molecular Sciences, vol. 16, pp. 8744-8760, 2015.
International Preliminary Report on Patentability, dated Jul. 23, 2019, in International Application No. PCT/JP2018/001667.
International Search Report & Written Opinion, dated Apr. 24, 2018, in International Application No. PCT/JP2018/001667.
Partial European Search Report dated Aug. 2, 2022 in European Application No. 22170264.0.
Alvarez-Fernández et al., A short CD/CD28 costimulation combined with IL-21 enhance the generation of human memory stem T cells for adoptive immunotherapy, Journal of Translational Medicine, vol. 14, pp. 1-10, 2016.
Onoda et al., Human CD4 central and effector memory T cells produce IL-21: effect on cytokine0diven proliferation of CD4 T cell subsets, International Immunology, vol. 19, No. 10, pp. 1191-1199, 2007.
Wölfl et al., Primed tumor-reactive multifunctional CD62L humanCD8 T cells for immunotherapy, Cancer Immunol Immunother, vol. 60, No. 2, pp. 173-186, 2011.
Notice of Reasons for Refusal mailed in the corresponding Japanese Application No. 2022-133779 dated Aug. 22, 2023 in 11 pages.

\* cited by examiner

METHOD FOR PRODUCING CD8alpha+beta+ CYTOTOXIC T CELLS

PRIORITY AND CROSS REFERENCE TO RELATED APPLICATIONS

This application is the U.S. National Stage Application under 35 U.S.C. § 371 of International Application No. PCT/JP2018/001667, filed Jan. 19, 2018, designating the U.S. and published as WO 2018/135646 A1 on Jul. 26, 2018, which claims the benefit of Japanese Patent Application No. JP 2017-008995, filed Jan. 20, 2017. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present invention relates to a method of producing $CD8\alpha^+\beta^+$ cytotoxic T lymphocytes, preferably a method of producing $CD8\alpha^+\beta^+$ cytotoxic T lymphocytes from pluripotent stem cells.

BACKGROUND ART

There is a possibility that cellular immunotherapy using cytotoxic T lymphocytes (CTLs) specific to disease-associated antigens may be very effective for controlling malignant tumors and chronic intractable infections. Conventionally, attempts have been made to produce antigen-specific CTLs in in vitro culture systems, but, since cell exhaustion inevitably occurs in in vitro culture systems, it has been difficult to prepare a sufficient number of antigen-specific CTLs, and therefore the therapeutic effects have been limited. However, with the recent advent of the induced pluripotent stem cell (iPSC) technology, a fundamental solution to the cell source problem is becoming available. In other words, a strategy for preparing iPSCs having infinite proliferative capacity from a small number of exhausted disease antigen-specific CTLs, and then allowing infinite regeneration of the CTLs in vitro, is becoming available.

For example, Patent Document 1 discloses a method of producing T cells, the method comprising the steps of: inducing hematopoietic progenitor cells from pluripotent stem cells; inducing CD4/CD8 double-positive cells from the hematopoietic progenitor cells; and inducing CD8-positive T cells from the CD4/CD8 double-positive cells.

Further, Patent Document 2 discloses a method of producing CD8-positive T cells, the method comprising: inducing CD4/CD8 double-positive T cells from pluripotent stem cells using a medium supplemented with vitamin C; and culturing the induced cells in a medium containing an adrenocortical hormone agent.

However, these methods cannot be said to be sufficient for production of cytotoxic T lymphocytes from pluripotent stem cells.

Further, Patent Document 3 and Non-patent Document 1 disclose that iPSCs were induced from human peripheral blood CTLs, and that hematopoietic progenitor cells were produced from the iPSCs, followed by co-culturing the produced cells with OP9/DLL1 cells expressing the Notch ligand DLL-1 in a medium containing IL (interleukin)-2, IL-7, and IL-15, to allow final differentiation into CTLs successfully.

PRIOR ART DOCUMENTS

Patent Documents

Patent Document 1: WO 2011/096482
Patent Document 2: WO 2016/076415
Patent Document 3: WO 2013/176197

Non-Patent Document

Non-patent Document 1: Cell Stem Cell. 2013 Jan. 3; 12(1):114-26.

SUMMARY

The redifferentiated CTLs disclosed in Patent Document 3 and Non-patent Document 1 had all of the CTL functions such as high cytotoxic activity, cytokine productivity, and proliferative capacity while retaining the antigen specificities of the original CTLs. However, it became clear that those cells also have NK cell-like properties, which are not found in normal CTLs. That is, while normal CTLs, including the original CTLs, belong to lymphocytes of the acquired immune system, the redifferentiated CTL had properties of lymphocytes of the innate immune system, to which NK cells belong. Among the properties of lymphocytes of the innate immune system found in the redifferentiated CTLs, the following are thought to especially strongly affect their clinical application: (1) a natural killer (NK) activity that injures targets non-antigen-specifically; (2) constant expression of activation molecules (such as NKp46) that induce the NK activity; (3) lower proliferative capacity and viability relative to those of normal CTLs of the acquired immune system; and (4) a decrease in the antigen recognition capacity caused by the fact that CD8, which is an accessory molecule of the antigen receptor, is a $CD8\alpha\alpha$ homodimer rather than the normal molecule, a $CD8\alpha\beta$ heterodimer. Regarding (1) and (2), effectiveness on escape variants can be expected, but, on the other hand, there is a risk of unexpected graft versus host disease (GVHD). Regarding (3), that is, the low proliferative capacity and viability, past reports have shown that insufficient in vivo persistency gives poor results in cellular immunotherapy. Further, regarding (4), the lack of expression of $CD8\alpha\beta$ needs to be solved since it leads directly to a decrease in the antigen recognition capacity of CTLs.

Since such properties of lymphocytes of the innate immune system are not necessarily suitable for cellular immunotherapy, an object of the present invention is to provide a method of efficiently producing CTLs having intrinsic properties of lymphocytes of the acquired immune system suitable for cellular immunotherapy.

The present inventors intensively studied to solve the above problems. As a result, by carrying out the step of culturing CD4/CD8 double-positive T cells in a medium containing IL-7 and a T-cell receptor activator, CTLs showing no NK activity and maintaining expression of $CD8\alpha\beta$ for a long period, that is, CTLs that are closer to normal CTLs of the acquired immune system, could be successfully prepared. Based on such findings, the present invention was completed.

More specifically, the present invention provides the following inventions.

[1] A method of producing CD8α⁺β⁺ cytotoxic T lymphocytes, the method comprising the step of:
culturing CD4/CD8 double-positive T cells in a medium containing IL (interleukin)-7 and a T-cell receptor activator, to induce CD8α⁺β⁺ cytotoxic T lymphocytes.

[2] The method according to [1], wherein the T-cell receptor activator is an anti-CD3 antibody.

[3] The method according to [1] or [2], wherein the medium further contains IL-21 and Flt3L (Flt3 ligand).

[4] The method according to any one of [1] to [3], comprising the following steps (a) and (b):
(a) culturing CD4/CD8 double-positive T cells in a medium containing IL-7 and a T-cell receptor activator; and
(b) culturing the cells obtained in step (a) in a medium containing IL-7, but not containing a T-cell receptor activator.

[5] The method according to [4], wherein the culture (b) is carried out using a culture vessel containing a fibronectin fragment and/or a Notch ligand.

[6] The method according to [5], wherein the fibronectin fragment is RetroNectin, and the Notch ligand is Delta-like 4 (DLL4).

[7] The method according to [5] or [6], further comprising the following step (c):
(c) culturing the cells obtained in step (b) in a medium containing IL-7, IL-21, and Flt3L using a culture vessel containing neither a fibronectin fragment nor a Notch ligand.

[8] The method according to [7], comprising the following steps (a1), (b1), and (c1):
(a1) culturing CD4/CD8 double-positive T cells in a medium containing IL-7, Flt3L, IL-21, and an anti-CD3 antibody;
(b1) culturing the cells obtained in step (a1) in a medium containing IL-7, Flt3L, and IL-21, but not containing an anti-CD3 antibody, using a culture vessel containing a fibronectin fragment; and
(c1) culturing the cells obtained in step (b1) in a medium containing IL-7, IL-21, and Flt3L using a culture vessel containing neither a fibronectin fragment nor a Notch ligand.

[9] The method according to [7], comprising the following steps (a2), (b2), and (c2):
(a2) culturing CD4/CD8 double-positive T cells in a medium containing IL-7, Flt3L, and an anti-CD3 antibody;
(b2) culturing the cells obtained in step (a2) in a medium containing IL-7 and Flt3L, but not containing an anti-CD3 antibody, using a culture vessel containing a fibronectin fragment and a Notch ligand; and
(c2) culturing the cells obtained in step (b2) in a medium containing IL-7, IL-21, and Flt3L using a culture vessel containing neither a fibronectin fragment nor a Notch ligand.

[10] The method according to any one of [1] to [9], wherein the culture is carried out without using feeder cells.

[11] The method according to any one of [1] to [10], further comprising the step of sorting the CD8α⁺β⁺ cytotoxic T lymphocytes obtained.

[12] The method according to [11], wherein the sorting step is carried out using as an index/indexes one or more of CD8β positivity, CD5 positivity, CD336 negativity, and CD1a negativity.

[13] The method according to any one of [1] to [12], further comprising the step of performing expansion culture of CD8α⁺β⁺ cytotoxic T lymphocytes in a medium containing IL-7, IL-15, and IL-21.

[14] The method according to any one of [1] to [12], further comprising the step of performing expansion culture of CD8α⁺β⁺ cytotoxic T lymphocytes in a medium containing IL-7 and IL-15, and one or more of IL-21, IL-18, IL-12, and TL1A.

[15] The method according to any one of [1] to [14], wherein the CD4/CD8 double-positive T cells are induced from pluripotent stem cells.

[16] The method according to [15], wherein the pluripotent stem cells are induced pluripotent stem (iPS) cells.

[17] The method according to [15] or [16], wherein the induction of the CD4/CD8 double-positive T cells from the pluripotent stem cells comprises the following steps (a) and (b):
(a) culturing the pluripotent stem cells in a medium supplemented with vitamin C, to induce hematopoietic progenitor cells; and
(b) culturing the hematopoietic progenitor cells obtained in step (a) in a medium containing vitamin C, FLT3L, and IL-7, to induce CD4/CD8 double-positive T cells.

[18] A method of producing CD8α⁺β⁺ cytotoxic T lymphocytes from pluripotent stem cells, the method comprising the steps of:
(a) culturing pluripotent stem cells in a medium supplemented with vitamin C, to induce hematopoietic progenitor cells;
(b) culturing the hematopoietic progenitor cells obtained in step (a) in a medium containing vitamin C, FLT3L, and IL-7, to induce CD4/CD8 double-positive T cells; and
(c) culturing the CD4/CD8 double-positive T cells obtained in step (b) in a medium containing IL-7 and a T-cell receptor activator, to induce CD8α⁺β⁺ cytotoxic T lymphocytes.

[19] The method according to [18], wherein the concentration of IL-7 in the medium in step (c) is higher than the concentration of IL-7 in the medium in step (b).

[20] The method according to any one of [1] to [19], wherein the CD8α⁺β⁺ cytotoxic T lymphocytes produced do not show natural killer (NK) activity.

[21] A culture of CD8α⁺β⁺ cytotoxic T lymphocytes obtained by the method according to any one of [1] to [20].

[22] A pharmaceutical composition comprising CD8α⁺β⁺ cytotoxic T lymphocytes obtained by the method according to any one of [1] to [20].

According to the present invention, CTLs which show no NK activity, which maintain expression of CD8c43 even during long-term culture, and which are closer to normal CTLs of the acquired immune system, can be prepared. The CTLs obtained by the method of the present invention exhibit higher antigen-specific cytotoxic activity, cytokine production, and proliferative capacity compared to those conventionally obtained. Further, the excellent characteristics of the CTLs obtained by the method of the present invention include not only the differentiation shift from lymphocytes of the innate immune system to those of the acquired immune system, but also maturation into naive/memory cells showing no cell exhaustion and maintenance characteristics of these cells. These CTLs have a remarkable proliferative capacity which enables expansion culture in vitro by a factor of not less than $10^{14}$. Thus, the present invention largely contributes to the current cellular immunotherapy, which has difficulty in obtaining the cells therefor.

DETAILED DESCRIPTION

Figure 1:
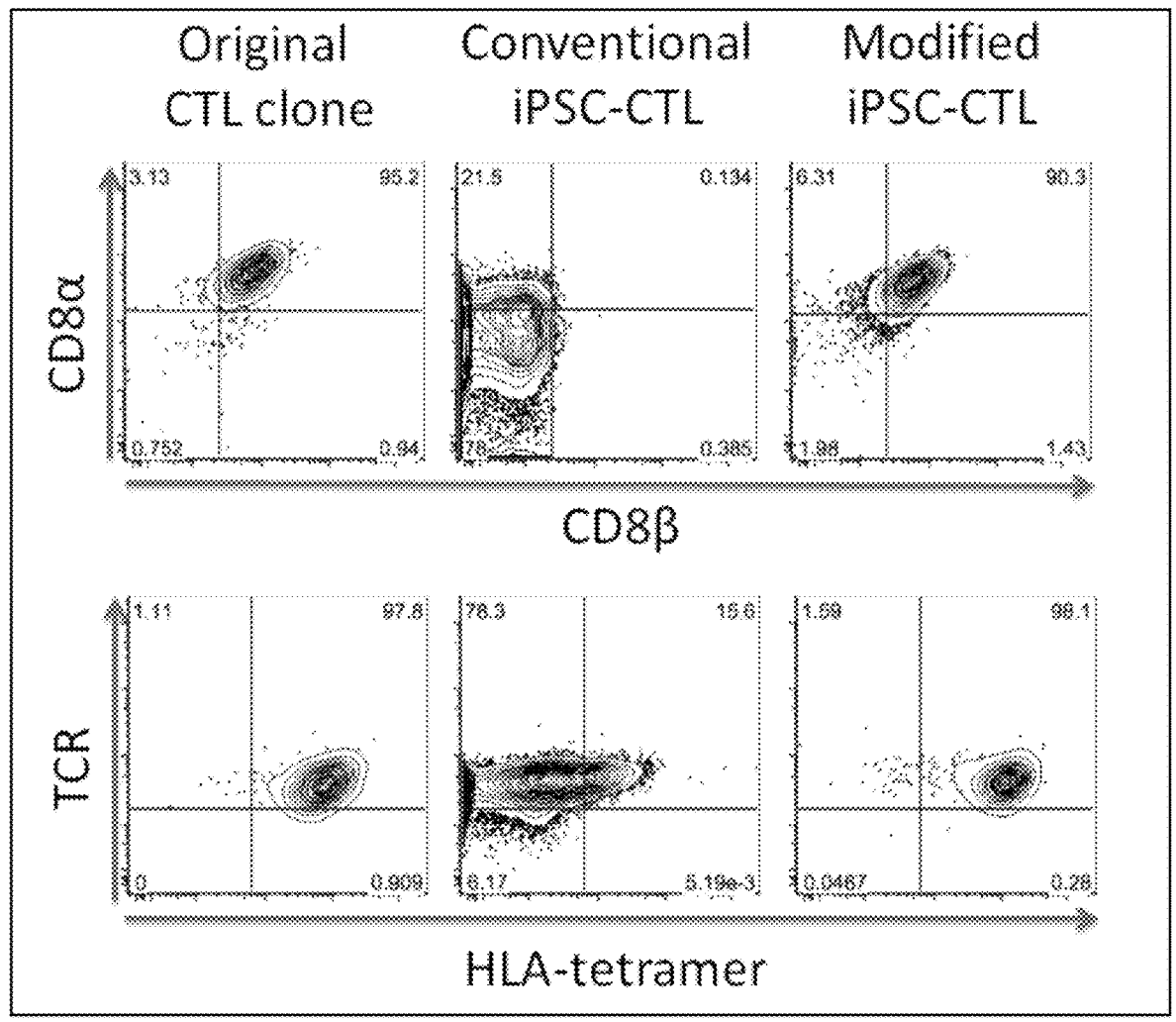
FIG. 1 shows the results of flow cytometry of modified (Modified) iPSC-CTLs prepared by the method of the present invention, the T cell clone used as the source of the iPS cells (Original CTL clone), and iPSC-CTLs prepared by a conventional method (conventional iPSC-CTL). The upper panel shows a diagram developed for CD8α and CD8β, and the lower panel shows a diagram developed for the staining intensities of TCR and HLA-tetramer.

The present invention provides a method of producing $CD8\alpha^+\beta^+$ cytotoxic T lymphocytes, the method comprising the step of:

culturing CD4/CD8 double-positive T cells in a medium containing IL-7 and a T-cell receptor activator, to induce $CD8\alpha^+\beta^+$ cytotoxic T lymphocytes.

In the present invention, the $CD8\alpha^+\beta^+$ cytotoxic T lymphocytes means T cells whose surface antigens CD8α and CD8β are both positive (wherein CD4 is negative), which T cells have cytotoxic activity.

Cytotoxic T lymphocytes (CTLs) recognize, through T-cell receptors (TCRs) present on the cell surface, antigen peptides derived from viruses, tumors, and the like presented together with class 1 major histocompatibility antigen (MHC class 1, HLA class 1) of antigen-presenting cells, to exert cytotoxic activity specifically to cells presenting the antigen peptides as foreign substances. The cytotoxic activity can be confirmed using as an index secretion or production of Granzyme, perforin, or the like.

On the other hand, CD4/CD8 double-positive T cells means T cells whose surface antigens CD4 and CD8 are both positive ($CD8^+CD4^+$). CD4/CD8 double-positive T cells can be induced to differentiate into CD4-positive cells ($CD8^-CD4^+$) or CD8-positive cells ($CD8^+CD4^-$). In the present invention, $CD8\alpha^+\beta^+$ cytotoxic T lymphocytes are induced from CD4/CD8 double-positive T cells.

The source of the CD4/CD8 double-positive T cells is not limited, and the CD4/CD8 double-positive T cells are preferably obtained by differentiation induction from pluripotent stem cells.

Pluripotent Stem Cells

In the present invention, the pluripotent stem cells are stem cells having pluripotency that allows differentiation into many kinds of cells present in a living body, which stem cells also have the proliferative capacity. The pluripotent stem cells include arbitrary cells which can be induced into CD4/CD8 double-positive T cells. Examples of the pluripotent stem cells include, but are not limited to, embryonic stem (ES) cells, embryonic stem cells derived from a cloned embryo obtained by nuclear transfer (ntES cells), germline stem cells ("GS cells"), embryonic germ cells ("EG cells"), induced pluripotent stem (iPS) cells, and pluripotent cells derived from cultured fibroblasts or bone marrow stem cells (Muse cells). The pluripotent stem cells are preferably iPS cells from the viewpoint of the fact that these cells can be obtained without destroying embryos, eggs, or the like during the production process. The pluripotent stem cells are more preferably human iPS cells.

Methods for producing iPS cells are known in the art. These cells can be produced by introducing reprogramming factors into somatic cells. Examples of the reprogramming factors herein include genes such as Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1, and gene products thereof. These reprogramming factors may be used individually, or may be used in combination. Examples of the combination of the reprogramming factors include those described in WO 2007/069666; WO 2008/118820; WO 2009/007852; WO 2009/032194; WO 2009/058413; WO 2009/057831; WO 2009/075119; WO 2009/079007; WO 2009/091659; WO 2009/101084; WO 2009/101407; WO 2009/102983; WO 2009/114949; WO 2009/117439; WO 2009/126250; WO 2009/126251; WO 2009/126655; WO 2009/157593; WO 2010/009015; WO 2010/033906; WO 2010/033920; WO 2010/042800; WO 2010/050626; WO 2010/056831; WO 2010/068955; WO 2010/098419; WO 2010/102267; WO 2010/111409; WO 2010/111422; WO 2010/115050; WO 2010/124290; WO 2010/147395; WO 2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat. Biotechnol. 26:1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat. Cell Biol. 11:197-203; R. L. Judson et al., (2009), Nat. Biotechnol., 27:459-461; Lyssiotis C A, et al. (2009), Proc Natl Acad Sci USA. 106:8912-8917; Kim J B, et al. (2009), Nature. 461:649-643; Ichida J K, et al. (2009), Cell Stem Cell. 5:491-503; Heng J C, et al. (2010), Cell Stem Cell. 6:167-74; Han J, et al. (2010), Nature. 463:1096-100; Mali P, et al. (2010), Stem Cells. 28:713-720; and Maekawa M, et al. (2011), Nature. 474:225-9.

Examples of the fetal somatic cells include any of fetal somatic cells, neonatal somatic cells, and mature, healthy or diseased somatic cells, as well as any of primary cultured cells, subcultured cells, and established cell lines.

In the present invention, for the purpose of use for production of CTLs, iPS cells are preferably produced using, as the somatic cells, lymphocytes (T cells) that have undergone gene rearrangement of T-cell receptor (TCR). In cases where lymphocytes are used as the somatic cells, the reprogramming step is preferably carried out after activation of the lymphocytes by stimulation with an anti-CD3 antibody and an anti-CD28 antibody in the presence of IL-2. Such stimulation can be carried out by, for example, culturing the lymphocytes for a predetermined period in a medium supplemented with IL-2, the anti-CD3 antibody, and the anti-CD28 antibody. Further, instead of adding these antibodies to the medium, the T cells may be stimulated by performing culture for a certain period on a culture dish having a surface to which the anti-CD3 antibody and the anti-CD28 antibody are bound. The stimulation may also be carried out by adding, to the medium, an antigen peptide that can be recognized by human T cells, together with feeder cells.

The CD8$\alpha^+\beta^+$ cytotoxic T lymphocytes produced in the present invention preferably have a desired antigen specificity. Thus, the lymphocytes used as the source of the iPS cells preferably have a desired antigen specificity, and the lymphocytes may be specifically isolated by purification using an affinity column or the like to which a desired antigen is immobilized. For example, a method in which lymphocytes having a desired antigen specificity are purified from a human tissue using a tetramer of MHC (major histocompatibility complex) (the so-called "MHC tetramer") to which a desired antigen is bound may also be employed.

The mammalian individual from which the somatic cells are collected is not limited. The mammalian individual is preferably human. In cases where CD8$\alpha^+\beta^+$ cytotoxic T lymphocytes prepared by the method of the present invention are used for cellular immunotherapy, the somatic cells used as the source of the iPS cells are preferably isolated from the subject to whom the CD8$\alpha^+\beta^+$ cytotoxic T lymphocytes are administered, from the viewpoint of easily matching the type of human leukocyte antigen (HLA) with the patient.

The method of obtaining the CD4/CD8 double-positive T cells from the pluripotent stem cells is not limited, and may be a known method. Examples of the method include those comprising the following steps (a) and (b):

(a) culturing pluripotent stem cells in a medium supplemented with vitamin C to induce hematopoietic progenitor cells; and (b) culturing the hematopoietic progenitor cells obtained in step (a) in a medium containing vitamin C, FLT3L, and IL-7, to induce CD4/CD8 double-positive T cells.

These steps are described below concretely. In the present invention, however, the method of inducing CD4/CD8 double-positive T cells from pluripotent stem cells is not limited to the following method.

Step of Inducing Hematopoietic Progenitor Cells from Pluripotent Stem Cells

In the present description, the hematopoietic progenitor cells (HPCs) are cells that are capable of differentiation into blood cells such as lymphocytes, eosinophils, neutrophils, basophils, erythrocytes, and megakaryocytes. Hematopoietic progenitor cells can be identified based on positivity of CD34 and/or CD43, which are surface antigens.

The hematopoietic progenitor cells can be produced by, for example, a method comprising the step of culturing pluripotent stem cells in a medium supplemented with vitamin C.

In the present invention, "vitamin C" means L-ascorbic acid or a derivative thereof, and "L-ascorbic acid derivative" means a derivative that becomes vitamin C by enzymatic reaction in a living body. Examples of the derivative of L-ascorbic acid include vitamin C phosphate, ascorbic acid glucoside, ascorbyl ethyl, vitamin C ester, ascorbyl tetrahexyldecanoate, ascorbyl stearate, and ascorbyl 2-phosphate 6-palmitate. The vitamin C is preferably vitamin C phosphate. Examples of the vitamin C phosphate include salts of L-ascorbic acid phosphate such as L-ascorbic acid phosphate Na and L-ascorbic acid phosphate Mg.

The medium used for the step of inducing hematopoietic progenitor cells is not limited. The medium may be prepared by adding vitamin C to a basal medium used for culture of animal cells. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixed media thereof. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines.

The basal medium is, for example, IMDM medium containing serum, insulin, transferrin, serine, thiol glycerol, L-glutamine, and ascorbic acid.

The medium used for the step of inducing hematopoietic progenitor cells may be further supplemented with a cytokine(s) selected from the group consisting of BMP4 (bone morphogenetic protein 4), VEGF (vascular endothelial growth factor), SCF (stem cell factor), and FLT3L (Flt3 ligand). The medium is more preferably a medium supplemented with VEGF, SCF, and FLT3L.

The amount of vitamin C added to the medium corresponds to, for example, 5 ng/ml to 100 µg/ml.

The amount of VEGF added to the medium corresponds to, for example, 10 ng/ml to 100 ng/ml.

The amount of SCF added to the medium corresponds to, for example, 10 ng/ml to 100 ng/ml.

The amount of FLT3L added to the medium corresponds to, for example, 1 ng/ml to 100 ng/ml.

In the step of inducing hematopoietic progenitor cells, the pluripotent stem cells may be cultured by adherent culture or suspension culture. In cases of adherent culture, the culture may be carried out in a culture vessel coated with a coating agent, and co-culture with other cells may be carried out. Examples of the other cells for the co-culture include C3H10T1/2 (Takayama N., et al. J Exp Med. 2817-2830, 2010) and stromal cells derived from a different species (Niwa A et al. J Cell Physiol. 2009 Nov.; 221(2): 367-77). Examples of the coating agent include Matrigel (Niwa A, et al. PLoS One. 6(7): e22261, 2011). Examples of the method of the suspension culture include the methods described in Chadwick et al. Blood 2003, 102: 906-15, Vijayaragavan et al. Cell Stem Cell 2009, 4: 248-62, and Saeki et al. Stem Cells 2009, 27: 59-67.

The hematopoietic progenitor cells may also be prepared from a net-like structure (which is also referred to as ES-sac or iPS-sac) obtained by culture of pluripotent stem cells. The "net-like structure" herein is a three-dimensional sac-shaped structure (having a space therein) derived from pluripotent stem cells. The structure is formed with an endothelial cell population and/or the like, and contains hematopoietic progenitor cells therein.

The temperature conditions for the step of inducing hematopoietic progenitor cells are not limited. The temperature is, for example, about 37° C. to about 42° C., preferably about 37 to about 39° C. The culture period is, for example, not less than 6 days. The culture may be carried out under hypoxic conditions. Examples of the hypoxic conditions include oxygen concentrations of 15%, 10%, 9%, 8%, 7%, 6%, and 5%, and oxygen concentrations lower than these.

The culture in the step of inducing hematopoietic progenitor cells may be carried out by appropriate combination of the above conditions. Examples of the combination include the steps of: (i) culturing pluripotent stem cells on C3H10T1/2 in a basal medium supplemented with vitamin C under hypoxic conditions; and (ii) further adding VEGF, SCF, and FLT3L to the medium of (i), and performing culture under normal oxygen conditions. The period of carrying out the step (i) is not less than 6 days, and the period of carrying out the step (ii) is not less than 6 days.

Step of Inducing CD4/CD8 Double-Positive T Cells from Hematopoietic Progenitor Cells In the present invention, the CD4/CD8 double-positive T cells can be induced by the step of culturing hematopoietic progenitor cells in a medium supplemented with vitamin C.

The medium used for the induction of the CD4/CD8 double-positive T cells is not limited. The medium may be prepared by adding vitamin C to a basal medium used for culture of animal cells. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixed media thereof. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines.

A preferred basal medium used for the induction of the CD4/CD8 double-positive T cells is αMEM medium containing serum, transferrin, serine, and L-glutamine. The type and the concentration of the vitamin C added to the basal medium are as described above for the case of the induction of the hematopoietic progenitor cells.

The medium used for the induction of the CD4/CD8 double-positive T cells in the present invention preferably further contains a cytokine selected from the group consisting of FLT3L and IL-7.

The concentration of IL-7 in the medium used for the induction of the CD4/CD8 double-positive T cells is, for example, 0.01 ng/ml to 100 ng/ml, preferably 0.1 ng/ml to 10 ng/ml.

The concentration of FLT3L in the medium used for the induction of the CD4/CD8 double-positive T cells is, for example, 1 ng/ml to 100 ng/ml.

In the production of the CD4/CD8 double-positive T cells, the hematopoietic progenitor cells may be cultured by adherent culture or suspension culture. In cases of adherent culture, a coated culture vessel may be used, and/or co-culture with feeder cells or the like may be carried out. Examples of the feeder cells for the co-culture include a bone-marrow stromal cell line, OP9 cells (available from Riken BioResource Center). The OP9 cells may be preferably OP-DL1 cells, which constantly express Dl11 (Holmes R1 and Zuniga-Pflucker J C. Cold Spring Harb Protoc. 2009(2)). In cases where OP9 cells are used as the feeder cells, Dl11, or a fusion protein of Dl11 and Fc or the like, separately provided may be added to the medium as appropriate to perform the co-culture. Examples of the Dl11 include: proteins encoded by genes having the nucleotide sequence of NCBI accession No. NM_005618 in cases of human, or NCBI accession No. NM_007865 in cases of mouse; and naturally occurring variants having high sequence identities (for example, having a sequence identity of not less than 90%) to these proteins and having equivalent functions. In cases where feeder cells are used for the production of the CD4/CD8 double-positive T cells, the feeder cells are preferably appropriately replaced during the culture. The replacement of the feeder cells may be carried out by transferring the subject cells during culture onto feeder cells that have been preliminarily plated.

The culture temperature conditions for the culture of the hematopoietic progenitor cells for the induction of the CD4/CD8 double-positive T cells are not limited. The temperature is, for example, about 37° C. to about 42° C., preferably about 37 to about 39° C. The culture period can be appropriately determined by those skilled in the art by monitoring of the number of the CD4/CD8 double-positive T cells and/or the like. The number of days is not limited as long as the CD4/CD8 double-positive T cells can be obtained. Examples of the number of days include not less than 10 days.

Step of Inducing $CD8\alpha^+\beta^+$ Cytotoxic T Lymphocytes from CD4/CD8 Double-Positive T Cells In the present invention, the $CD8\alpha^+\beta^+$ cytotoxic T lymphocytes can be produced by culturing CD4/CD8 double-positive T cells in a medium containing IL-7 and a T-cell receptor activator. This step is preferably adherent culture, and the culture is preferably carried out without using feeder cells. It is preferred to carry out the culture in a state where the CD4/CD8 double-positive T cells directly adhere to a culture vessel coated with a fibronectin fragment and/or a Notch ligand.

The concentration of IL-7 in the medium used for the induction of the $CD8\alpha^+\beta^+$ cytotoxic T lymphocytes is preferably higher than the concentration of IL-7 in the medium used for the "Step of Inducing CD4/CD8 Double-positive T Cells from Hematopoietic Progenitor Cells". The concentration is, for example, 0.05 ng/ml to 500 ng/ml, preferably 0.1 ng/ml to 100 ng/ml, more preferably 0.5 ng/ml to 50 ng/ml.

Examples of the T-cell receptor activator include PHA (phytohaemagglutinin), anti-CD3 antibody, anti-CD28 antibody, PMA, and ionomycin.

For example, an anti-CD3 antibody or the like may be added to the medium followed by culturing the CD4/CD8 double-positive T cells for a certain period, to stimulate the T-cell receptor (TCR). The anti-CD3 antibody or the like may have magnetic beads or the like bound thereto. Instead of adding the antibody to the medium, the T-cell receptor may be stimulated by culturing the T cells on a culture dish having a surface to which an anti-CD3 antibody is bound. Such a case also corresponds to the culture in a medium containing a TCR activator. In the stimulation of the TCR of the CD4/CD8 double-positive T cells, the concentration of the anti-CD3 antibody to be bound to the surface of the culture dish is not limited. The concentration is, for example, 0.1 to 100 µg/ml.

Preferably, the T-cell receptor activator is included into the medium together with IL-7 when the "Step of Inducing $CD8\alpha^+\beta^+$ Cytotoxic T Lymphocytes from CD4/CD8 Double-positive T Cells" begins, and, preferably after 1 or 2 days of culture, the medium is replaced with a medium containing IL-7 but not containing a T-cell receptor activator (wherein, for example, the concentration of the T-cell receptor activator is less than 1 ng/ml or under the detection limit), followed by continuation of the culture. In such a case, a culture vessel coated with a fibronectin fragment and/or a Notch ligand is preferably used at the time of the replacement with the medium not containing a T-cell receptor activator.

Thereafter, more preferably, the culture is further carried out preferably in a medium containing IL-7, IL-21, and Flt3L using a culture vessel containing neither a fibronectin fragment nor a Notch ligand (that is, a culture vessel not coated with these).

The medium used for the step of inducing $CD8\alpha^+\beta^+$ cytotoxic T lymphocytes is not limited, and may be prepared by using a medium used for culture of animal cells as a basal medium, and adding IL-7, a TCR activator, and/or the like thereto. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixed media thereof. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines. A preferred basal medium is αMEM medium containing serum, transferrin, serine, L-glutamine, and ascorbic acid.

The medium used for the step of inducing $CD8\alpha^+\beta^+$ cytotoxic T lymphocytes preferably further contains a cytokine other than IL-7, or vitamin C Examples of the cytokine include FLT3L and IL-21. The medium preferably does not contain IL-15 (for example, the concentration of IL-15 is less than 1 ng/ml or under the detection limit). By the use of a medium not containing IL-15, maturation of lymphocytes of the innate immune system, which have higher requirement of IL-15, can be suppressed, so that efficient induction of CTLs, which have the properties of lymphocytes of the acquired immune system, is possible. Further, the medium used for the step of inducing $CD8\alpha^+\beta^+$ cytotoxic T lymphocytes may contain a caspase inhibitor. Examples of the caspase inhibitor include Pan Caspase fmk Inhibitor Z-VAD.

The type and the concentration of the vitamin C used for the induction of the $CD8\alpha^+\beta^+$ cytotoxic T lymphocytes are as described above for the case of the induction of the hematopoietic progenitor cells.

The concentration of FLT3L in the medium used for the induction of the $CD8\alpha^+\beta^+$ cytotoxic T lymphocytes is, for example, 1 ng/ml to 100 ng/ml.

The concentration of IL-21 in the medium used for the induction of the $CD8\alpha^+\beta^+$ cytotoxic T lymphocytes is, for example, 1 ng/ml to 100 ng/ml.

In the present invention, the Notch ligand means a substance which binds to a Notch signal receptor to activate a Notch signal. The Notch signal receptor means a single-pass transmembrane protein that is a heterodimer composed of NECD and TM-NICD, which is produced by cleavage of a Notch receptor composed of an extracellular domain (NECD), a transmembrane domain (TM), and an intracellular domain (NICD) into the TM-NICD by processing. Examples of the ligand of the Notch signal receptor include members of the Delta-like family (DLL1, DLL3, DLL4) and the Jagged family (JAG1, JAG2). The ligand of the Notch signal receptor may be a recombinant, or a fusion protein with Fc or the like. For example, it is commercially available from Adipogen, and can be easily used. The ligand of the Notch signal receptor used in the present invention is preferably DLL4 or JAGE In the present invention, the fibronectin (FN) fragment is selected from fragments contained in the FN-binding domain, cell adhesion domain, or heparin-binding domain. For example, at least one fragment selected from $III_1$, $III_2$, $III_3$, $III_7$, $III_8$, $III_9$, $III_{11}$, $III_{12}$, $III_{13}$, and CS-1 may be contained. Further, the fragment may be a fragment in which a plurality of domains are repeatedly linked to each other.

For example, a fragment containing a cell adhesion domain containing a ligand for VLA-5, a heparin-binding domain, a CS-1 domain that is a ligand for VLA-4, III$_1$, or the like may be used in the present invention. Examples of the fragment include CH-271, CH-296, H-271, and H-296 described in J. Biochem., vol. 110, pp, 284 to 291 (1991), and derivatives and modified products thereof. The CH-296 is commercially available under the name of RetroNectin (registered trademark). A polypeptide corresponding to the ⅔-portion in the C-terminal side of III$_1$ is also commercially available under the name of Fibronectin Fragment III$_1$-C.

The FN fragment may be used in a state where it is immobilized on an appropriate solid phase, for example, a carrier for cell culture such as cell culture equipment, bead, membrane, or slide glass. The immobilization of the FN fragment on the solid phase can be carried out by, for example, the method described in WO 00/09168. The concentration of the FN fragment used in the present invention is not limited. For example, it is added to the medium such that the final concentration is 0.001 to 500 μg/ml, preferably 0.01 to 500 μg/ml. In cases where the FN fragment is used by immobilization, immobilization to a solid phase may be carried out using a FN fragment solution having the above concentration. Culturing of a cell population in the presence of a FN fragment is described in detail in WO 03/080817, and the culture may be carried out with reference thereto.

The Notch ligand may also be used by immobilization on cell culture equipment, and the concentration and the method therefor are also as described above.

In the present invention, the temperature conditions for the culture of the CD4/CD8 double-positive T cells for the induction of the CD8α$^+$β$^+$ cytotoxic T lymphocytes are not limited. The temperature is, for example, about 37° C. to about 42° C., preferably about 37 to about 39° C. The culture period can be appropriately determined by those skilled in the art by monitoring of the number of the CD8-positive T cells and/or the like. The number of days is not limited as long as the CD8α$^+$β$^+$ cytotoxic T lymphocytes can be obtained. Examples of the number of days include not less than 1 day.

Step of Expansion Culture of CD8α$^+$β$^+$ Cytotoxic T Lymphocytes

By subjecting the thus obtained CD8α$^+$β$^+$ cytotoxic T lymphocytes to expansion culture, a large amount of CD8α$^+$β$^+$ cytotoxic T lymphocytes can be obtained. The expansion culture can be carried out using a medium containing, for example, IL-7, IL-15, and IL-21. Alternatively, the expansion culture can be carried out using a medium containing, in addition to IL-7 and IL-15, one or more of IL-21, IL-18, IL-12, and TL1A (TNF-like ligand 1A; another name, vascular endothelial growth inhibitor (VEGI) or TNF superfamily member 15 (TNFSF15)).

Preferably, the cells obtained from the CD4/CD8 double-positive T cells are further subjected to sorting of CD8α$^+$β$^+$ cytotoxic T lymphocytes using FACS, an affinity column, or the like, and then the sorted cells are subjected to the above expansion culture. The sorting may be carried out using as an index/indexes one or more of CD8β positivity, CD5 positivity, CD336 negativity, and CD1a negativity. Since CD8β is an auxiliary receptor of TCR, sorting for CD8β positivity enables sorting of CTLs having high antigen recognition capacity, and moreover, elimination of abnormal NK-like cells. By carrying out sorting using CD5 positivity as an index, cells stably expressing CD8β and having high proliferative capacity can be sorted. Further, since CD1a is a marker for immature T cells, immature cells can be eliminated by sorting using CD1a negativity as an index.

Further, since CD336 is a marker which is not expressed in normal CTLs, and which is expressed only in cells of the innate immune system, abnormal NK-like cells can be eliminated by sorting using CD336 negativity as an index.

In the present invention, the medium used for the step of expansion culture of the CD8α$^+$β$^+$ cytotoxic T lymphocytes is not limited, and may be prepared by using a medium used for culture of animal cells as a basal medium, and adding a cytokine(s) such as IL-7, IL-15, and IL-21 thereto. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixed media thereof. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines. A preferred basal medium is αMEM medium containing serum, transferrin, serine, L-glutamine, and ascorbic acid.

The medium used for the step of expansion culture of the CD8α$^+$β$^+$ cytotoxic T lymphocytes preferably further contains an anti-CD3 antibody and vitamin C.

In the present invention, the type and the concentration of the vitamin C used for the step of expansion culture of the CD8α$^+$β$^+$ cytotoxic T lymphocytes are as described above.

The concentration of IL-7 in the medium used for the step of expansion culture of the CD8α$^+$β$^+$ cytotoxic T lymphocytes is, for example, 1 ng/ml to 100 ng/ml.

The concentration of IL-15 in the medium used for the step of expansion culture of the CD8α$^+$β$^+$ cytotoxic T lymphocytes is, for example, 1 ng/ml to 100 ng/ml.

The concentration of IL-21 in the medium used for the step of expansion culture of the CD8α$^+$β$^+$ cytotoxic T lymphocytes is, for example, 1 ng/ml to 100 ng/ml.

The concentration of IL-12 in the medium used for the step of expansion culture of the CD8α$^+$β$^+$ cytotoxic T lymphocytes is, for example, 1 ng/ml to 100 ng/ml.

The concentration of IL-18 in the medium used for the step of expansion culture of the CD8α$^+$β$^+$ cytotoxic T lymphocytes is, for example, 1 ng/ml to 100 ng/ml.

The concentration of TL1A in the medium used for the step of expansion culture of the CD8α$^+$β$^+$ cytotoxic T lymphocytes is, for example, 1 ng/ml to 100 ng/ml.

The anti-CD3 antibody is not limited as long as it is an antibody that specifically recognizes CD3. Examples of the anti-CD3 antibody include the antibody produced from OKT3 clone. The concentration of the anti-CD3 antibody in the medium is, for example, 10 ng/ml to 10 μg/ml. Instead of adding the anti-CD3 antibody to the medium, the anti-CD3 antibody may be immobilized on the culture vessel. The anti-CD3 antibody may be removed during the expansion culture.

In the present invention, the temperature conditions for the step of expansion culture of the CD8α$^+$β$^+$ cytotoxic T lymphocytes are not limited. The temperature is, for example, about 37° C. to about 42° C., preferably about 37 to about 39° C. The culture period can be appropriately determined by those skilled in the art by monitoring of the number of the CD8α$^+$β$^+$ cytotoxic T lymphocytes and/or the like. The number of days is not limited as long as the CD8α$^+$β$^+$ cytotoxic T lymphocytes can be obtained.

Examples of the number of days include not less than 5 days. In the expansion culture step, IL-7 and IL-15 are preferably present in the medium throughout the expansion culture step. On the other hand, regarding IL-21, IL-18, IL-12, and TL1A, as long as they are present in the medium during the initial phase of the expansion culture step (for example, from the beginning to Hour 12, Hour 16, Hour 24, or Hour 72 of the expansion culture), they do not need to be contained in the medium thereafter.

In such culture, the $CD8\alpha^+\beta^+$ cytotoxic T lymphocytes may be co-cultured with feeder cells. The feeder cells are not limited. From the viewpoint of further promoting maturation and proliferation of the $CD8\alpha^+\beta^+$ cytotoxic T lymphocytes through cell contact and the like, the feeder cells are preferably peripheral blood mononuclear cells (PBMCC).

The expansion culture step is applicable also to T cells other than cells derived from pluripotent stem cells, for example, T cells isolated from a T cell clone or a living body. Thus, the present invention provides a method of allowing proliferation of T cells, comprising the step of culturing T cells in a medium containing IL-7 and IL-15, and one or more of IL-21, IL-18, IL-12, and TL1A. Further, the present invention provides a medium for culturing T cells, containing IL-7 and IL-15, and one or more of IL-21, IL-18, IL-12, and TL1A. The T cells as mentioned herein are preferably cytotoxic T lymphocytes, more preferably $CD8\alpha^+\beta^+$ cytotoxic T lymphocytes. As described above, the T cells are not limited to T cells other than cells derived from pluripotent stem cells, and may also be T cells isolated from a T cell clone or a living body.

<Pharmaceutical Composition Comprising $CD8\alpha^+\beta^+$ Cytotoxic T Lymphocytes, Cellular Immunotherapy>

The $CD8\alpha^+\beta^+$ cytotoxic T lymphocytes (culture) produced by the method of the present invention have an antigen-specific cytotoxic activity as shown in the Examples below. Thus, the $CD8\alpha^+\beta^+$ cytotoxic T lymphocytes, preferably human $CD8\alpha^+\beta^+$ cytotoxic T lymphocytes, produced by the method of the present invention are useful for treatment or prevention of diseases such as tumors, infections (for example, chronic infections), and autoimmune deficiency.

Accordingly, the present invention provides a pharmaceutical composition comprising $CD8\alpha^+\beta^+$ cytotoxic T lymphocytes produced by the method of the present invention, and a cellular immunotherapy using the $CD8\alpha^+\beta^+$ cytotoxic T lymphocytes.

In the cellular immunotherapy of the present invention, the administration of the T cells ($CD8\alpha^+\beta^+$ CTLs) to the subject to be treated may be, but does not need to be, preferably parenteral administration such as intravenous, intraperitoneal, subcutaneous, or intramuscular administration, more preferably intravenous administration. The administration may also be topical administration to an affected area.

The pharmaceutical composition of the present invention can be prepared by subjecting the $CD8\alpha^+\beta^+$ cytotoxic T lymphocytes produced by the method of the present invention to formulation by a known pharmaceutical method. For example, the pharmaceutical composition may be used, mainly parenterally, as a capsule, solution, film-coated agent, suspension, emulsion, injection solution (such as a solution for intravenous injection or drip infusion), or the like.

These may be formulated as appropriate by combination with, for example, a pharmaceutically acceptable carrier or medium, more specifically, sterile water or physiological saline, vegetable oil, solvent, base, emulsifier, suspending agent, surfactant, stabilizer, vehicle, antiseptic, binder, diluent, isotonic agent, soothing agent, bulking agent, disintegrator, buffer, coating agent, lubricant, coloring agent, solubilizer, or other additives. Further, known pharmaceutical compositions, immunostimulants, and the like used for treatment or prevention of the above diseases may be used in combination.

When the pharmaceutical composition of the present invention is administered, the dose is appropriately selected according to, for example, the age, body weight, symptoms, and health conditions of the subject, and the type of the composition (for example, whether the composition is a pharmaceutical or food or beverage).

The cellular immunotherapy using the $CD8\alpha^+\beta^+$ cytotoxic T lymphocytes of the present invention comprises the steps of: isolating T cells having a desired antigen specificity from a human; inducing iPS cells from the T cells having a desired antigen specificity; allowing the iPS cells to differentiate into CD4/CD8 double-positive T cells; allowing the CD4/CD8 double-positive T cells to differentiate into $CD8\alpha^+\beta^+$ cytotoxic T lymphocytes; and administering the resulting $CD8\alpha^+\beta^+$ cytotoxic T lymphocytes into a body of a mammal such as a human.

When the cellular immunotherapy is carried out, from the viewpoint of prevention of rejection reaction, the subject from which the T cells are to be isolated preferably has the same HLA type as the subject to which the $CD8\alpha^+\beta^+$ cytotoxic T lymphocytes obtained by the present invention are to be administered. The subject from which the T cells are to be isolated is more preferably the same as the subject to which the $CD8\alpha^+\beta^+$ cytotoxic T lymphocytes obtained by the present invention are to be administered. Regarding the cells to be administered, the $CD8\alpha^+\beta^+$ cytotoxic T lymphocytes produced by the method of the present invention may be administered as they are, or the cells may be administered in the form of a pharmaceutical composition formulated as described above.

EXAMPLES

The present invention is described below more concretely by way of Examples. However, the scope of the present invention is not limited to these Examples.

<Preparation of $CD8\alpha\beta$+CTLs>

Cells iPS cells (TKT3v 1-7 line) were established using the method described in Nishimura T, et al., Cell Stem Cell. 12(1): 114-126, 2013 from human CD3-positive T cells isolated with informed consent.

C3H10T1/2 cells and OP9/DLL1 cells were obtained from Riken BioResource Center.

K562/HLA A-24 was provided by Dr. Tachikawa at Tokyo University (currently at National Institute of Infectious Diseases).

Induction of CD4/CD8 Double-Positive Cells (DP Cell Induction Step)

On confluent C3H10T1/2 cells in a 10-cm dish, a small cluster of the TKT3v 1-7 line was plated (Day 0), and the cells were cultured for 7 days under hypoxic conditions (5% $O_2$) in EB medium (IMDM supplemented with 15% fetal bovine serum (FBS), 10 µg/ml human insulin, 5.5 µg/ml human transferrin, 5 ng/ml sodium selenite, 2 mM L-glutamine, 0.45 mM α-monothioglycerol, and 50 µg/ml phospho ascorbic acid) (Day 7).

Subsequently, 20 ng/ml VEGF, 30 ng/ml SCF, and 10 ng/ml FLT3L (manufactured by Peprotech) were added, and culture was performed under normal oxygen pressure conditions for 7 days (Day 14).

Hematopoietic cells contained in the resulting net-like structure (which is also referred to as iPS-SAC) (CD34$^+$ hematopoietic progenitor cells) were collected, and then plated on OP9/DLL1 cells. The cells were then cultured in OP9 medium (αMEM supplemented with 15% FBS, 2 mM L-glutamine, 100 U/ml penicillin, 50 μg/ml phospho ascorbic acid, 100 ng/ml streptomycin, 5.5 μg/ml human transferrin, and 5 ng/ml sodium selenite) supplemented with 10 ng/ml FLT3L and 1 ng/ml IL-7, under normal oxygen pressure conditions for 23 days (Day 37). The cells were plated onto fresh OP9/DLL1 cells every 3 to 4 days.

Differentiation Induction from CD4/CD8 Double-Positive Cells (Maturation Step) (Protocol 1)

On Day 37, while the co-culture of OP9/DLL1 and the differentiated cells was maintained, αMEM medium containing 20% FBS, PSG (penicillin-streptomycin-L-glutamine), ITS (insulin-transferrin-sodium selenite), 50 μg/ml phospho ascorbic acid, 10 μM Pan Caspase fmk Inhibitor Z-VAD (FMK001, R&D), 10 ng/ml IL-7, 20 ng/ml IL-21, 10 ng/ml Flt3L, and 2 μg/ml anti-human CD3 antibody (OKT3) was added.

On Day 38, the medium was completely washed away, and, after transferring the cells to a plate coated with 5 μg/ml Retronectin (Takara Bio Inc.), culture was carried out. The medium used was the same as the medium for Day 37 except that the anti-CD3 antibody was not included. The culture vessel coated with Retronectin was prepared by placing their solutions in a culture vessel and leaving the culture vessel to stand at 4° C. overnight, followed by washing with PBS.

On Day 41, the medium was replaced with the medium having the same composition as the medium for Day 38 except that the IL-21 concentration was 10 ng/ml. The culture was further continued after transferring the cells to a plate coated with neither Fc-DLL4 nor Retronectin.

The cells were collected on Day 43, and sorted for CD8β$^+$CD336$^-$CD5$^+$CD1a$^-$ cells by FACS.

Feeder-Free Expansion Culture (Expansion Culture 1)

In a 96-well flat bottom plate, 1 μg/ml anti-CD3 antibody (OKT3) prepared by dilution with PBS was placed, and the plate was then left to stand at 4° C. overnight to provide an OKT3-coated plate. The CD8β$^+$CD5$^+$CD1a$^-$ cells obtained as described above were suspended in αMEM medium containing 20% FBS, PSG, ITS, 50 μg/ml phospho ascorbic acid, 5 ng/ml IL-7, 5 ng/ml IL-15, and 10 ng/ml IL-21, and then transferred to the OKT3-coated plate, followed by performing culture for 16 hours.

The cells were then transferred to a well not coated with OKT3, and the culture was continued while performing half-medium changes at 3-day intervals thereafter. In all medium changes, the components other than IL-21 were always added in the same amounts. IL-21 was added at 5 ng/ml only in the first medium change.

The cells on Day 14 to Day 21 after the beginning of the expansion culture were subjected to the following experiment as CD8α$^+$β$^+$ CTLs (modified iPSC-CTLs).

As a control for comparison, CTLs obtained by differentiation induction by a conventional protocol (conventional CTLs) were used. The conventional protocol employed was a method in which expansion culture is carried out directly after the DP cell induction step, without carrying out a maturation step.

Feeder-Free Expansion Culture (Expansion Culture 2)

In a 96-well flat bottom plate, 1 μg/ml anti-CD3 antibody (OKT3) prepared by dilution with PBS was placed, and the plate was then left to stand at 4° C. overnight to provide an OKT3-coated plate. The CD8β$^+$CD5$^+$CD1a$^-$ cells obtained as described above were suspended in αMEM medium containing 20% FBS, PSG, ITS, 50 μg/ml phospho ascorbic acid, 10 μM Pan Caspase fmk Inhibitor Z-VAD (FMK001, R&D), 5 ng/ml IL-7, 5 ng/ml IL-15, 20 ng/ml IL-21, 50 ng/ml IL-12, 50 ng/ml IL-18, and 50 ng/ml TL1A (2×10$^4$ cells/200 μl/well), and then transferred to the OKT3-coated plate, followed by performing culture for 16 hours.

The cells were then transferred to a well not coated with OKT3, and the culture was continued while performing half-medium changes at 3-day intervals thereafter. In the medium changes, αMEM medium containing 20% FBS, PSG, ITS, 50 μg/ml phospho ascorbic acid, 5 ng/ml IL-7, and 5 ng/ml IL-15 was used. The cells on Day 14 after the beginning of the expansion culture were subjected to the following experiment as CD8α$^+$β$^+$ CTLs (modified iPSC-CTLs).

<Evaluation of CD8α$^+$β$^+$ CTLs>

1. Analysis of Expression of CD8αβ and Antigen-Binding Capacity

The modified iPSC-CTLs prepared by the method of the present invention, the conventional CTLs prepared by the conventional method, and the original CTLs used as the source of the iPS cells were investigated for expression of CD8α and CD8β using a flow cytometer. As a result, as shown in the upper panel of FIG. 1, the modified iPSC-CTLs were found to show stable expression of CD8αβ even after repeated expansion culture. Further, the antigen-binding capacities of TCRs of the above cells were quantified by the tetramer method. As a result, as shown in the lower panel of FIG. 1, the level of binding of the modified iPSC-CTLs prepared by the method of the present invention to the HLA-tetramer was as high as that of the original CTLs. On the other hand, in spite of almost the same level of expression of TCRs, the conventional CTLs obtained by the conventional method showed remarkably weak binding to the HLA-tetramer because of the absence of expression of CD8β.

2. Analysis of Cell Proliferation and Cytokine Production

Subsequently, the modified iPSC-CTLs (Modified CD8b+ CTL) and the conventional iPSC-CTLs (conventional CD8b$^-$ CTL) were stained with CFSE, and stimulated with K562/HLA A-24 presenting 0 (Unpulsed), 10 nM, or 100 nM specific antigen peptide (Nef138-8).

Decay of CFSE due to proliferation, and production of the two kinds of cytokines IFNγ and IL-2 were investigated. CFSE is a reagent used for proliferation assays since its fluorescence intensity decreases each time proliferation occurs (J Vis Exp. 2010; (44): 2259) (the higher the number of times of proliferation, the lower the CFSE fluorescence from the cells).

Figure 2:
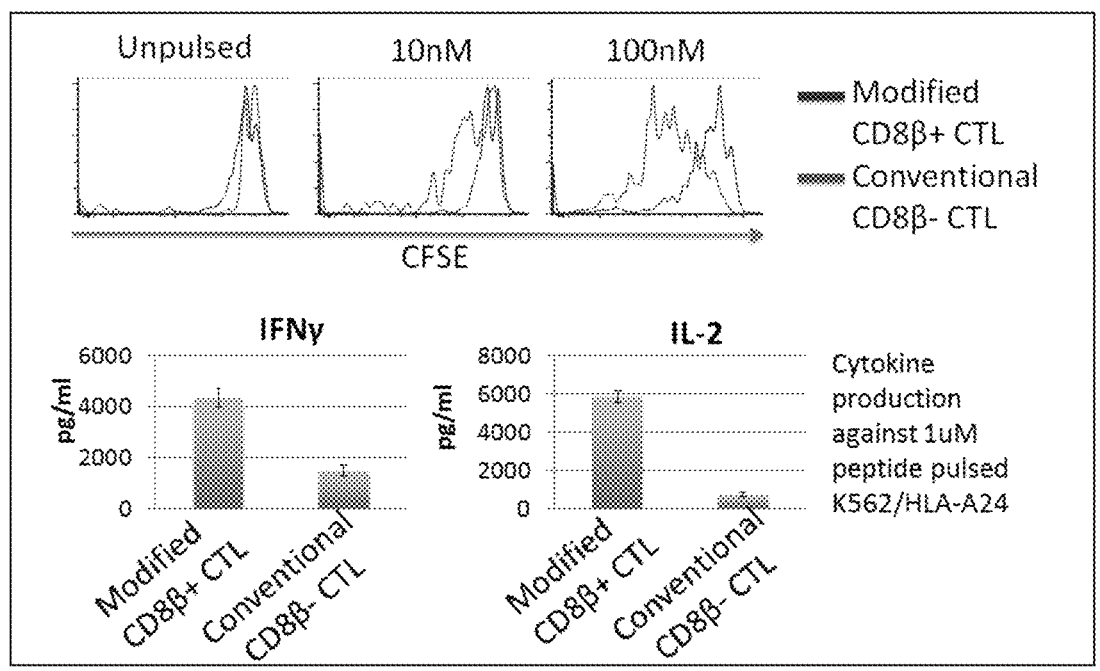
FIG. 2 shows a diagram illustrating the proliferative capacities of modified iPSC-CTLs prepared by the method of the present invention (Modified CD8b+ CTL) and conventional iPSC-CTLs (conventional CD8b− CTL) as investigated by staining the cells with CFSE and stimulating the cells with K562/HLA A-24 presenting a specific antigen peptide (upper panel; the ordinate represents the number of cells, and the abscissa represents the CFSE fluorescence intensity), and the results of investigation of production of the two cytokines IFNγ and IL-2 (lower panel).

The results are shown in FIG. 2. In the CFSE assay, the modified iPSC-CTLs showed a higher proliferative capacity than the conventional CTLs. Further, the modified CTLs also showed a much higher cytokine productivity.

3. Analysis of Cytotoxic Activity

Figure 3:
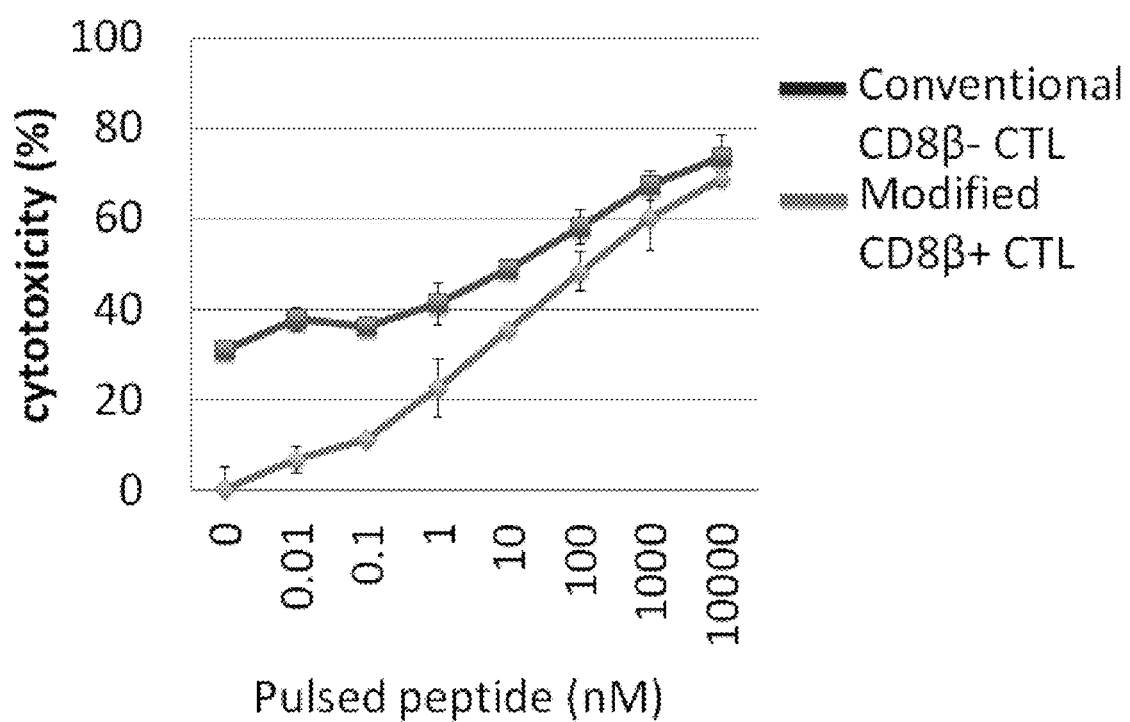
FIG. 3 shows a diagram illustrating association between the amount of antigen peptide and the cytotoxic activity observed when modified iPSC-CTLs prepared by the method of the present invention (Modified CD8b+ CTL) and conventional iPSC-CTLs (conventional CD8b− CTL) were co-cultured with K562/HLA A-24 pulsed with a specific antigen peptide.

The modified iPSC-CTLs (Modified CD8b$^+$ CTL) or the conventional iPSC-CTLs (Conventional CD8b− CTL) were co-cultured with K562/HLA A-24 pulsed with various concentrations of a specific antigen peptide (Nef138), and the cytotoxic activity was investigated using the LDH activity as an index. The results are shown in FIG. 3. While the modified iPSC-CTLs showed disappearance of the NK activity, they had a better antigen-specific cytotoxic activity compared to the conventional CTLs. Thus, both showed equivalent levels of cytotoxic activity to the target cells presenting a sufficient amount of antigen.

4. Analysis of Cell Characteristics

Figure 4:
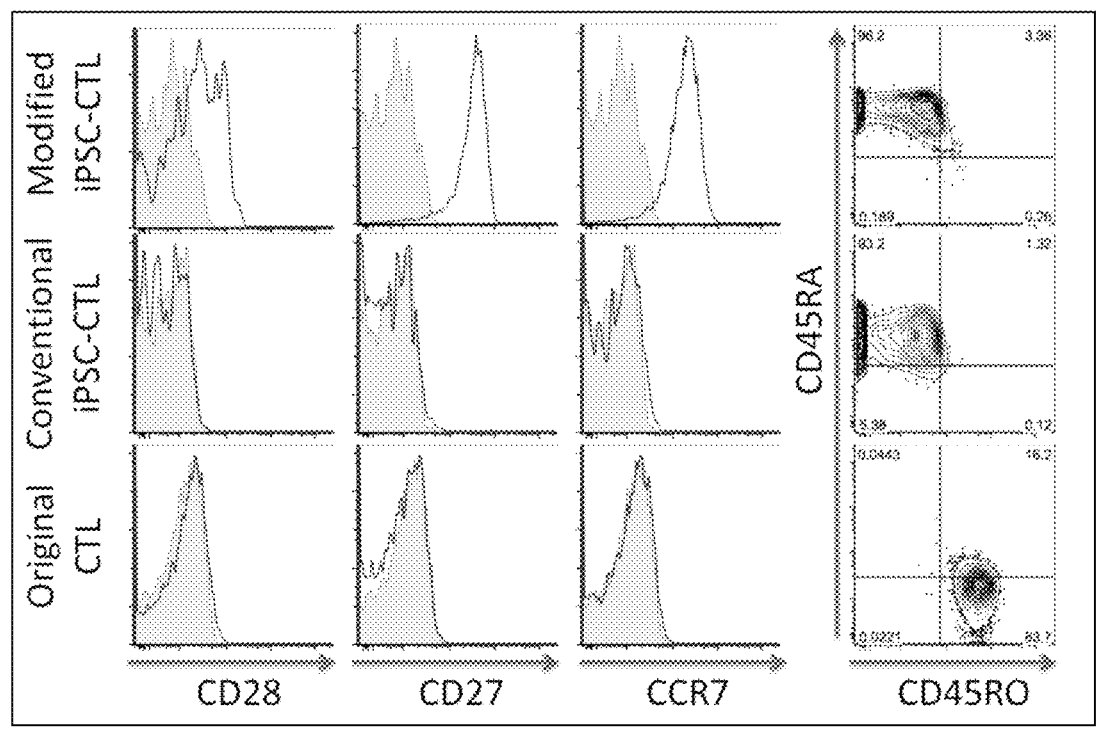
FIG. 4 shows results of FACS analysis of modified iPSC-CTLs prepared by the method of the present invention (Modified CD8b+ CTL), conventional iPSC-CTLs (conventional CD8b− CTL), and the original T cell clone, for CD28, CD27, and CCR7 (left), and results of FACS analysis for the combination of CD45RA and CD45RO (right).

The modified iPSC-CTLs (Modified CD8b$^+$ CTL), the conventional iPSC-CTLs (conventional CD8b$^-$ CTL), and the original T cell clone were analyzed by FACS. CD28 and CD27 are costimulators expressed only in naive or central memory cells, and CCR7 is a homing molecule indispensable for immune surveillance. All of these are functional molecules directly linked to the CTL function. As shown in FIG. 4, while expression of these molecules disappeared in the original CTLs during the ex vivo culture, recovery of the expression was found only in the modified iPSC-CTLs. Further, regarding the combination of CD45RA and CD45RO, which is most frequently used for distinguishing between naive cells and memory cells, both the modified and conventional iPSC-CTLs showed CD45RA$^+$CD45RO$^-$, which is characteristic to naive cells.

5. Analysis of Proliferative Capacity in Expansion Culture

Figure 5:
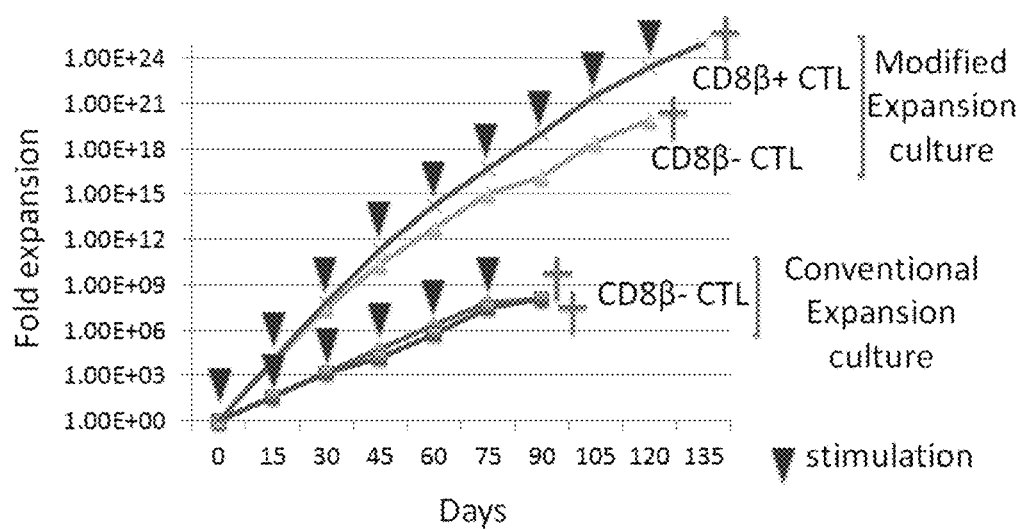
FIG. 5 shows results of analysis of proliferation of modified iPSC-CTLs prepared by the method of the present invention (Modified CD8b+ CTL) and conventional iPSC-CTLs (conventional CD8b− CTL) (the day when expansion culture started is represented as Day 0).

The modified iPSC-CTLs (Modified CD8b$^+$ CTL) prepared by the method of the present invention (Expansion Culture 1) and the conventional iPSC-CTLs (conventional CD8b$^-$ CTL) were analyzed for their proliferation. As shown in FIG. 5, in a modified on-feeder expansion culture system containing αMEM as a basal medium, and also containing ITS and phospho ascorbic acid as supplements, the modified iPSC-CTLs showed an extremely high proliferative capacity of not less than $10^{20}$.

Figure 6:
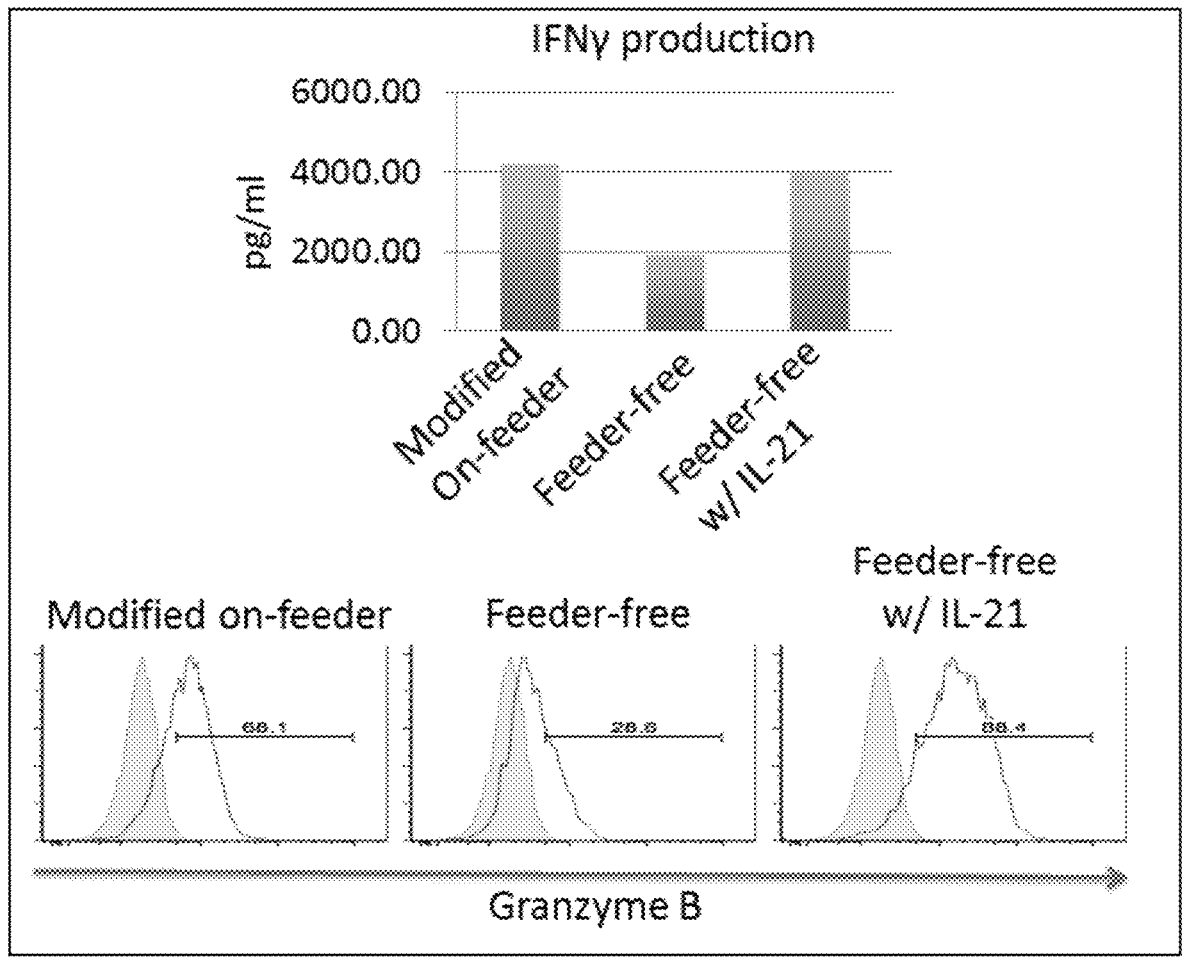
FIG. 6 shows results obtained by stimulating modified iPSC-CTLs prepared by the method of the present invention (Modified CD8b+ CTL) in the presence of PHA+PBMC or no feeder cells (with or without addition of IL-21), and quantifying the production of a cytokine (IFNγ) and the expression level of a cytotoxic molecule (Granzyme B).

6. Analysis of IFNγ Production and Expression Level of Cytotoxic Molecule in Expansion Culture The modified iPSC-CTLs (Modified CD8b$^+$ CTL) prepared by the method of the present invention (Expansion Culture 1) were stimulated in the presence of PHA+PBMC or no feeder cells (with or without addition of IL-21), and the production of the cytokine IFNγ and the expression level of the cytotoxic molecule Granzyme B were quantified. As shown in FIG. 6, it became clear that addition of IL-21 in feeder-free expansion culture promotes not only production of the cytokine, but also expression of Granzyme B, so that the functionality can be maintained similarly to the on-feeder method.

Figure 7:
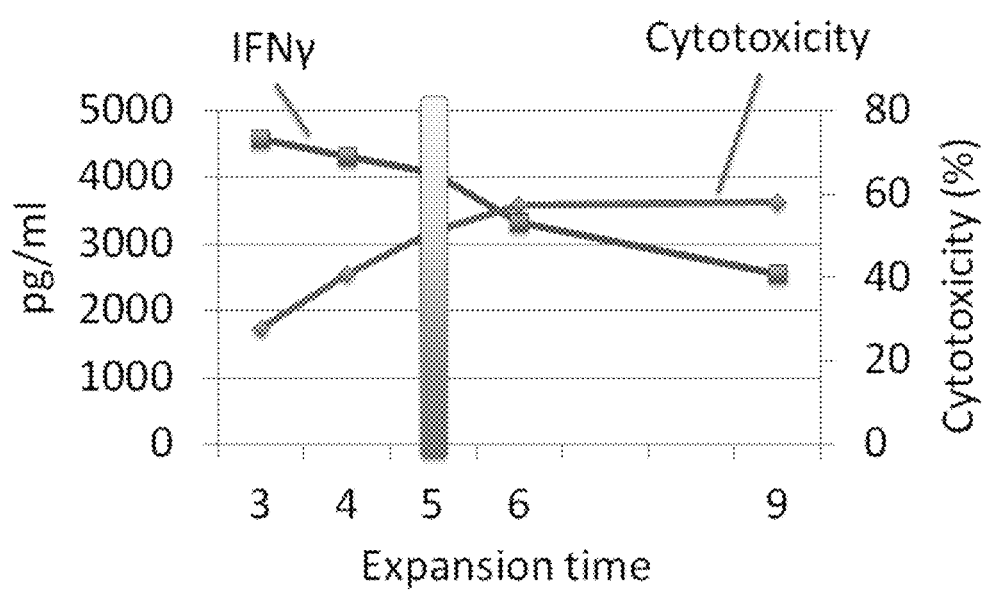
FIG. 7 shows results obtained by measuring the production of a cytokine (IFNγ) and the cytotoxic activity of modified iPSC-CTLs prepared by the method of the present invention (Modified CD8b+ CTL).

7. Analysis of Cytokine Production and Cytotoxic Activity Under Antigen Stimulation The modified iPSC-CTLs (Modified CD8b+ CTL) prepared by the method of the present invention (Expansion Culture 1) were stimulated with PHA+PBMC, and their cytokine production and cytotoxic activity were investigated. As shown in FIG. 7, as the stimulation was repeatedly carried out, possibly because of the naive phenotype, the modified iPSC-CTLs acquired cytotoxic activity while losing the IFNγ production capacity.

8. Analysis of Cytokine Production and Expression of Cytotoxic Molecule

Figure 8:
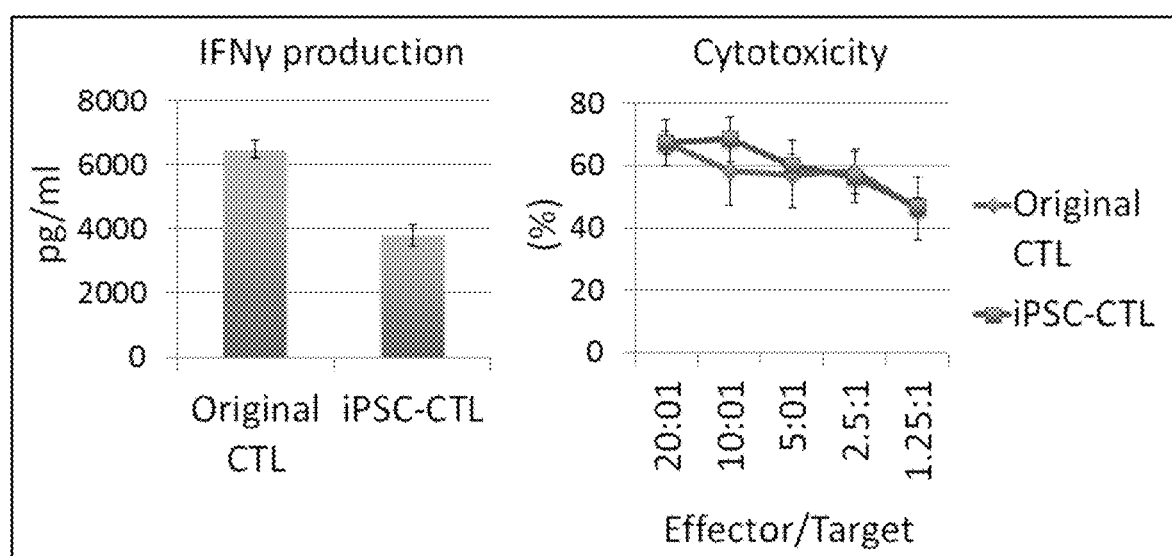
FIG. 8 shows results obtained by quantifying the cytokine production and the expression level of the cytotoxic molecule in modified iPSC-CTLs prepared by the method of the present invention (Modified CD8b+ CTL) and original CTLs.

The modified iPSC-CTLs (Modified CD8b+ CTL) prepared by the method of the present invention (Expansion Culture 1) and the original CTLs were stimulated with PHA+PBMC. At the timing of Expansion time: 5 in FIG. 7, the production of the cytokine IFNγ and the expression level of the cytotoxic molecule Granzyme B were quantified. As shown in FIG. 8, iPSC-CTLs prepared by the combination of on-feeder and feeder-free expansion cultures as expected in clinical application were compared with the original CTLs in terms of the function. As a result, it became clear that both have equivalent cytotoxic activities although the former CTLs have a rather weaker cytokine production capacity.

Figure 9:
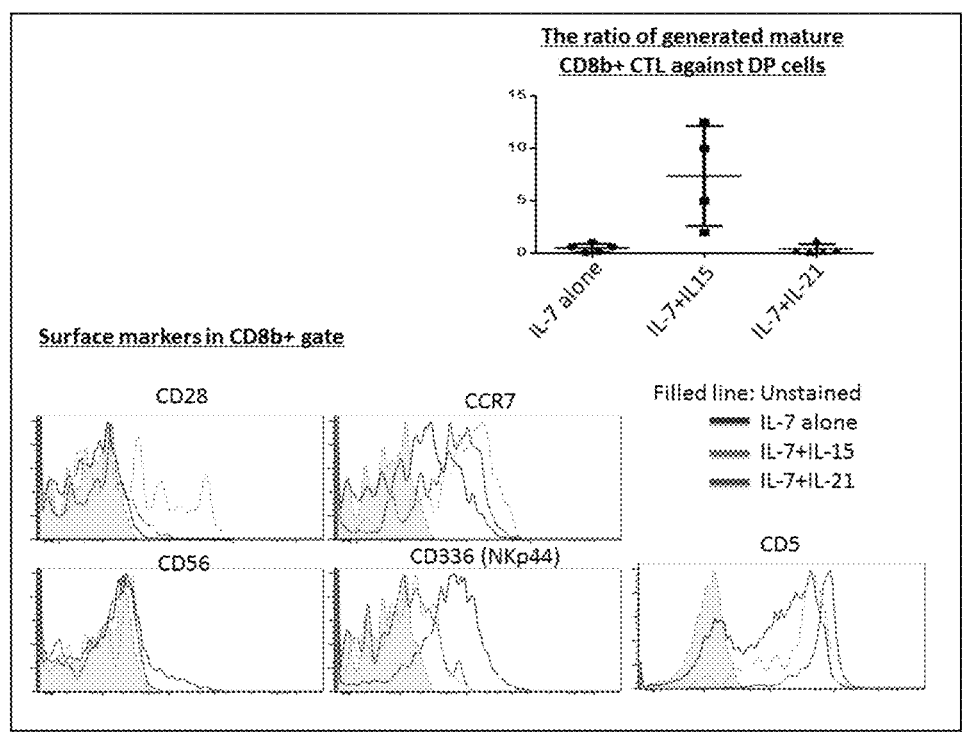
FIG. 9 shows results of analysis of the effect of addition of IL-7 and IL-21 on the production of $CD8\alpha^+\beta^+$ CTLs and surface markers.

9. Analysis of Effect of Addition of IL-7 and IL-21 on Production of CD8α$^+$β$^+$ CTLs and Surface Markers The effect of addition of IL-15 and IL-21 in the iPSC-CTL maturation process was studied. The results are shown in FIG. 9. The upper graph in FIG. 9 shows the production efficiency of CD8α$^+$β$^+$ CTLs against DP cells. It can be seen that the production efficiency of CD8α$^+$β$^+$ CTLs drastically increased by the addition of IL-15.

However, in the lower panel of FIG. 9, it can be seen that the addition of IL-15 led to remarkable decreases in the expression of CCR7, which is both a representative marker of naive CTLs and an important chemokine receptor, and CD5, which is thought to be associated with the proliferative capacity. Further, CD56 and CD336, which are NK markers not expressed in normal CTLs, were induced by the addition of IL-15. Thus, it was suggested that, although IL-15 increases the production efficiency of CD8α$^+$β$^+$ CTLs, the resulting cells do not have the original desirable properties of CTLs.

On the other hand, although the addition of IL-21 did not show contribution to the production efficiency of CD8α$^+$β$^+$ CTLs, no side effect increasing NK-associated markers was found, and moreover, an effect that promotes expression of CCR7, and CD28, which is an important costimulator, was found.

10. Analysis of Cytokine Production Profile of Prepared iPSC-CTLs

Figure 10:
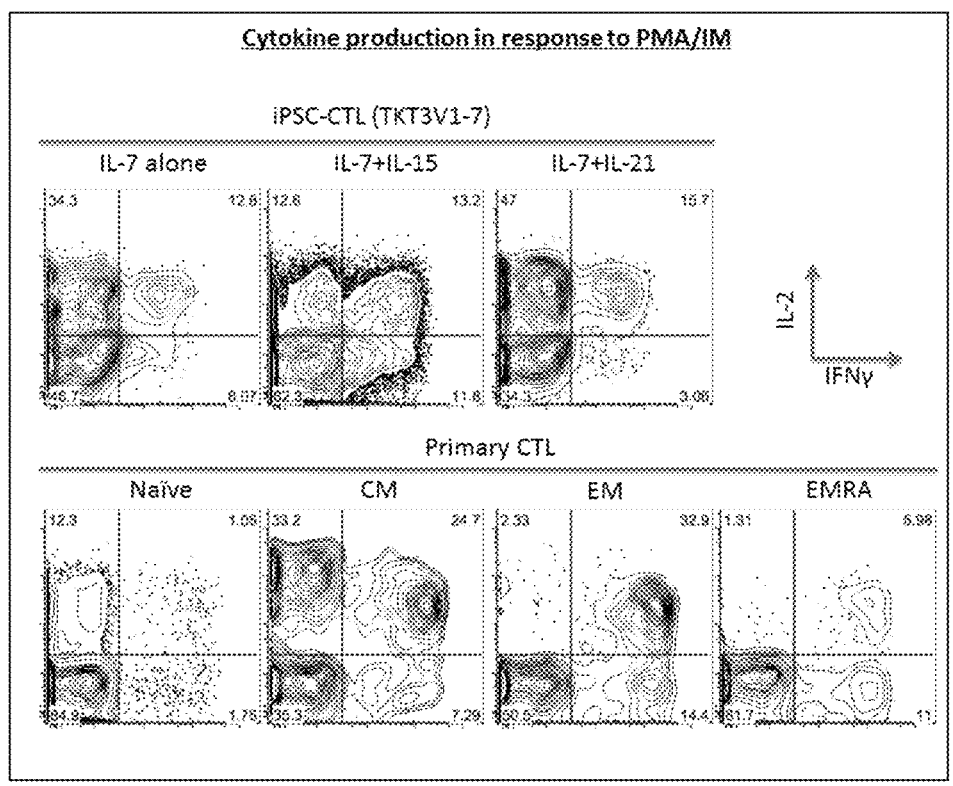
FIG. 10 shows results of analysis of the cytokine production profiles of prepared iPSC-CTLs and primary CTLs.

According to a past report, it is known that mature CTLs change their IL-2 and IFNγ production profiles during the process of differentiation from naive to central memory (CM), effector memory (EM), and then EMRA cells, which are most differentiated cells. The closer the cells are to naive cells, the more the cells shift to production of IL-2. As the differentiation proceeds, cells producing IFNγ at the same time, and cells producing only IFNγ appear. Here, an important point is that naive cells, which are less differentiated than the more differentiated EM and EMRA, are well known to exhibit a stronger antitumor effect in vivo. As shown in FIG. 10, the IL-2/IFNγ profile of the modified iPSC-CTLs prepared by the method of the present invention corresponded to an intermediate between naive and CM, exhibiting an extremely high IL-2 production capacity as is the case with less differentiated cells. From this result, it is suggested that the iPSC-CTLs have naive/CM-like characteristics and high antitumor activity.

Further, from the result of FIG. 9, it was suggested that the preparation of naive CTLs was inhibited by the addition of IL-15. In accordance with this fact, it was found that the addition of IL-15 led to a decrease in the IL-2 production capacity. On the other hand, the addition of IL-21 had an effect that increases the IL-2 production.

Thus, taking the results in FIGS. 9 and 10 into account as a whole, it was suggested that addition of IL-21 is especially useful for maturation culture of iPSC CTLs.

11. Another Mode of Maturation Step

Differentiation Induction from CD4/CD8 Double-Positive Cells (Maturation Step) (Protocol 2)

After the DP cell induction step, on Day 37, while the co-culture of OP9/DLL1 and the differentiated cells was maintained, αMEM medium containing 20% FBS, PSG (penicillin-streptomycin-L-glutamine), ITS (insulin-transferrin-sodium selenite), 50 µg/ml phospho ascorbic acid, 10

μM Pan Caspase fmk Inhibitor Z-VAD (FMK001, R&D), 10 ng/ml IL-7, 10 ng/ml Flt3L, and 2 μg/ml anti-human CD3 antibody (OKT3) was added.

On Day 38, the medium was completely washed away, and, after transferring the cells to a plate coated with 5 μg/ml Retronectin (Takara Bio Inc.) and 1 μg/ml Fc-DLL4 (Sino Biological Inc.), culture was carried out. The medium used was the same as the medium for Day 37 except that the anti-CD3 antibody was not included. The culture vessel coated with Fc-DLL4 and Retronectin was prepared by placing their solutions in a culture vessel and leaving the culture vessel to stand at 4° C. overnight, followed by washing with PBS.

On Day 44, the medium was replaced with the medium which was the same as the medium for Day 38 except that IL-21 was further added at 10 ng/ml. The culture was further continued after transferring the cells to a plate coated with neither Fc-DLL4 nor Retronectin.

The cells were collected on Day 58, and sorted for CD8β+ CD336⁻CD5⁺CD1a⁻ cells by FACS.

Figure 11:
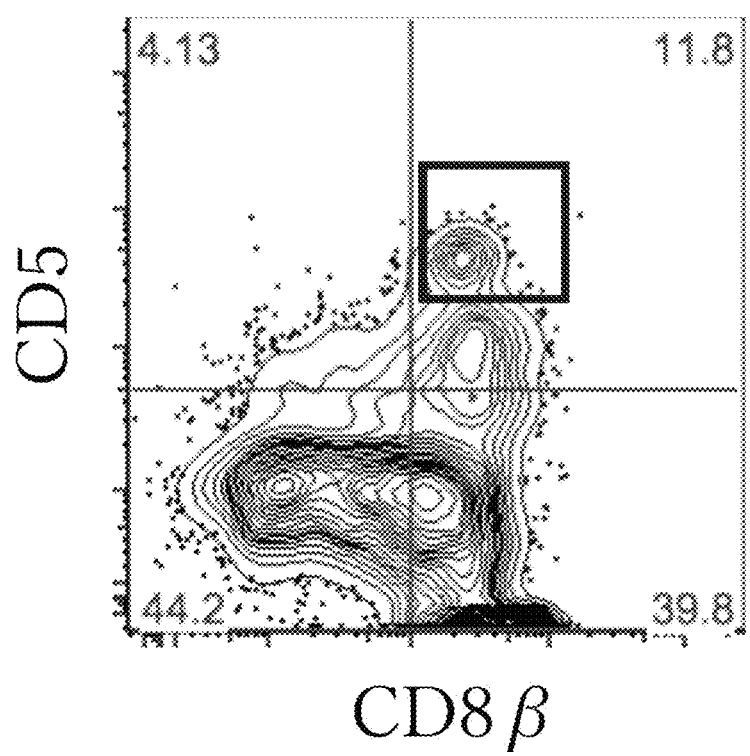
FIG. 11 shows a result obtained by sorting CD8β/CD5 double-positive cells from iPSC-CTLs maturated by a conventional method, carrying out PHA on-feeder expansion culture for 2 weeks, and then performing FACS analysis.
Figure 12:
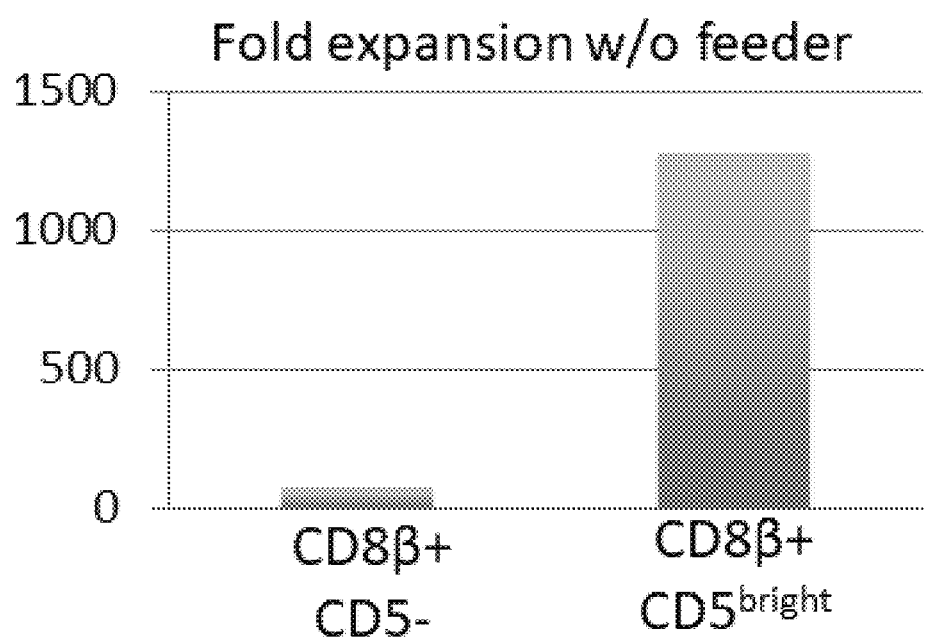
FIG. 12 shows results obtained by dividing conventional-method iPSC-CTLs after expansion culture into CD8β+ CD5bright cells and CD8β+CD5− cells, carrying out the second expansion culture under feeder-free conditions, and then performing analysis of the proliferative capacity.

12. Comparison of Marker Expression and Proliferative Capacity Between Conventional iPSC-CTLs and Modified iPSC-CTLs FIG. 11 shows a FACS result obtained after sorting CD8β/CD5 double-positive cells from iPSC-CTLs maturated by a conventional method, and then carrying out PHA on-feeder expansion culture for 2 weeks. In the conventional iPSC-CTLs, even though the culture was started with the CD8β/CD5 double-positive cells, expression of both molecules largely decreased by the single time of expansion culture because of low expression stability (especially in CD5). Further, when the cells after the initial expansion culture were divided into CD8β⁺CD5$^{bright}$ cells and CD8β⁺CD5⁻ cells, and the second expansion culture was carried out under feeder-free conditions, the CD8b⁺CD5$^{bright}$ cells were found to show a much higher proliferative capacity than the CD8b⁺CD5⁻ cells (FIG. 12). This is consistent with a past report which showed that CD5 can be used as an index of highly proliferative CTLs (Nature Immunology, 16.1 (2015), 107-117.). From these results, it was suggested that, although production of highly proliferative CD5$^{bright}$ iPSC-CTLs is possible by the conventional method, the efficiency and stability of the method are very low, and production of CD⁵⁻ cells with a low proliferative capacity mainly occurs in most cases.

Figure 13:
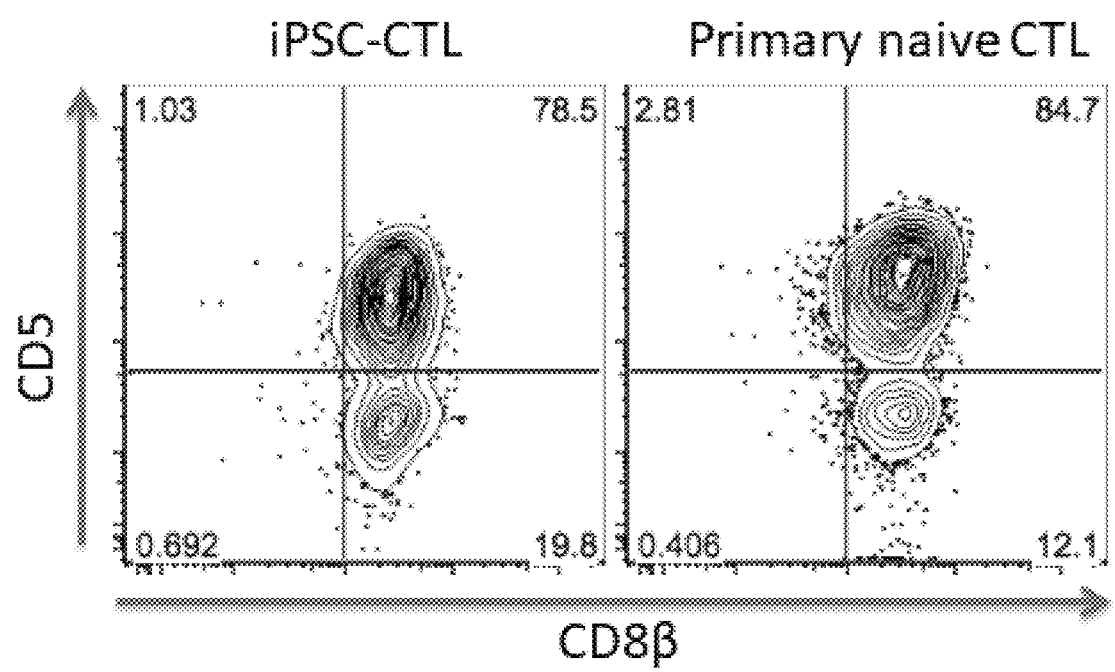
FIG. 13 shows results obtained by sorting CD8β/CD5 double-positive cells from modified iPSC-CTLs, carrying out PHA on-feeder expansion culture four times, and then performing FACS analysis.
Figure 14:
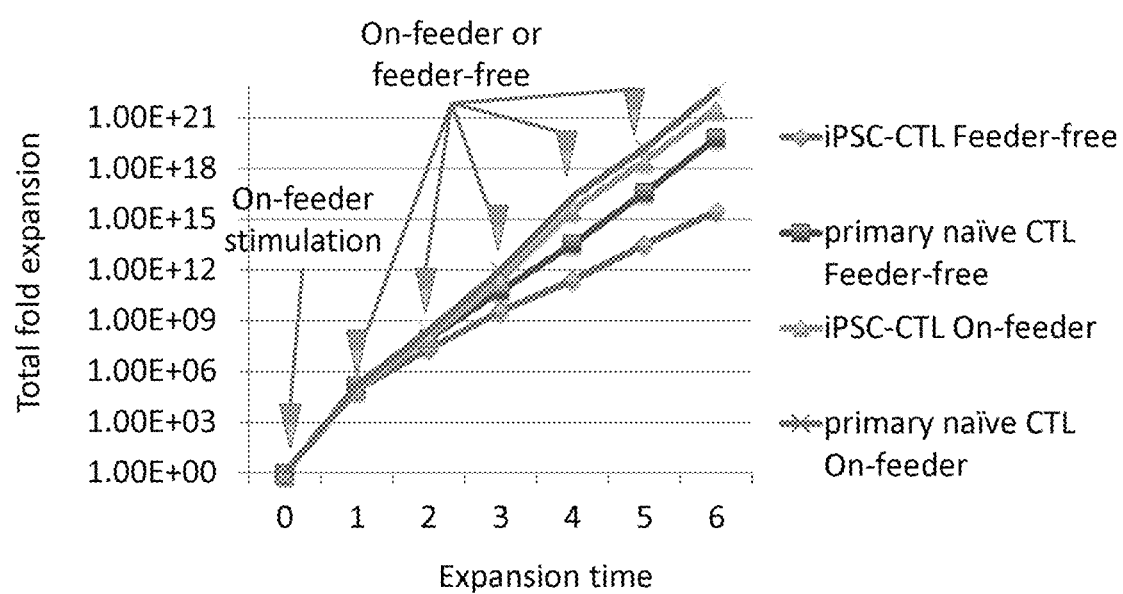
FIG. 14 shows results of analysis of proliferation of modified iPSC-CTLs and naive CTLs in expansion culture with or without feeders.

On the other hand, the modified iPSC-CTLs induced by the protocol 2 showed high expression of CD5 from immediately after the maturation, and a high expression level equivalent to that of the primary CTLs could be maintained even after four times of expansion culture (FIG. 13). In accordance with this result, by the continuous stimulation of the modified iPSC-CTLs, proliferation occurred by a factor of more than $10^{20}$ in the on-feeder case, and more than $10^{15}$ even in the feeder-free case in total. Thus, although the proliferative capacities were lower than those of the primary naive CTLs, extremely high proliferative capacities suitable for clinical application could be observed (FIG. 14).

13. Analysis of Proliferative Capacity in Expansion Culture

Figure 15:
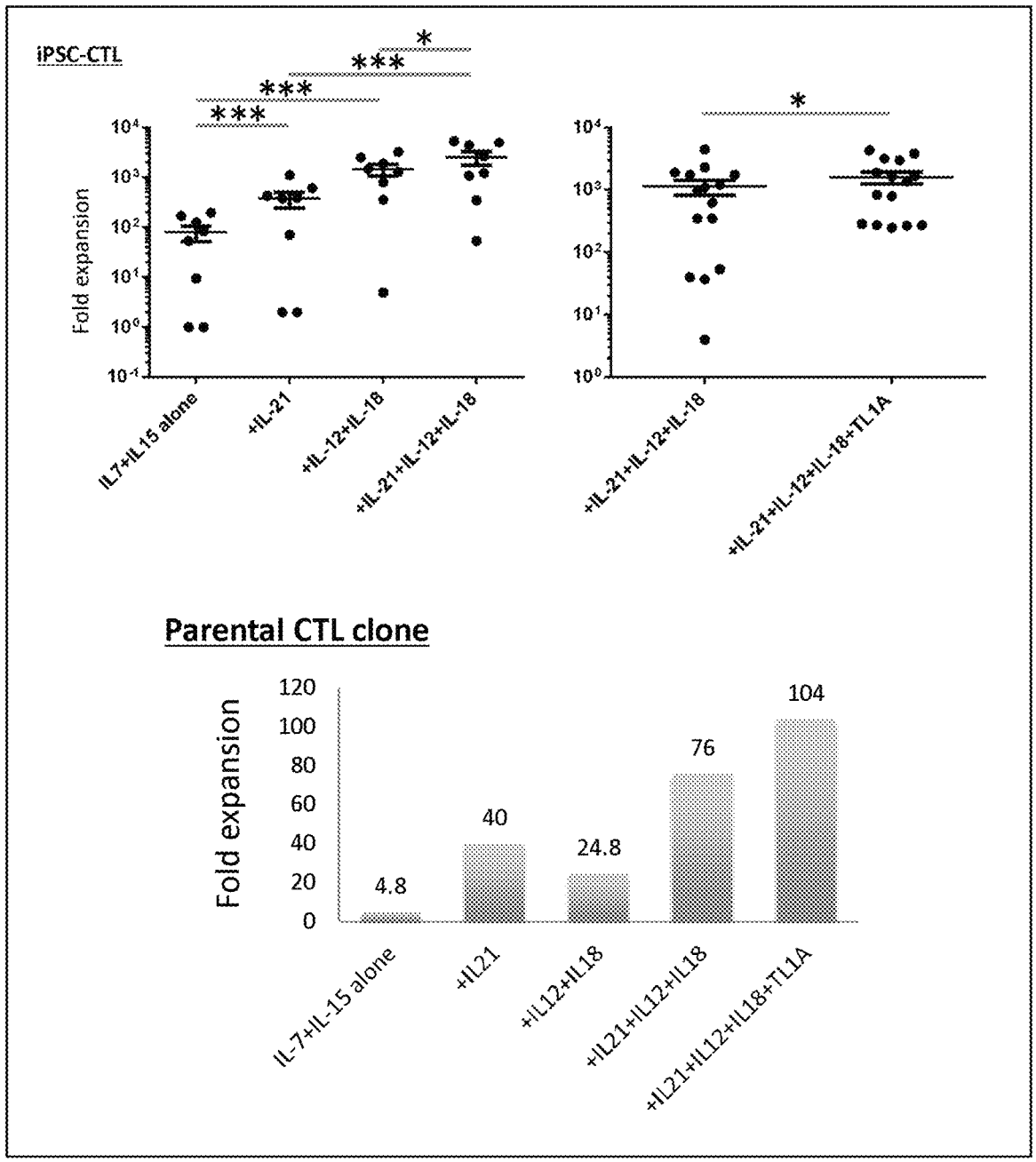
FIG. 15 shows results of analysis of proliferation of modified iPSC-CTLs (Modified CD8b+ CTL) and the parental CTL clone (H25-4) in 2-week expansion culture in media containing cytokines (represented as the rate of increase from the beginning of the expansion culture).

The modified iPSC-CTLs (Modified CD8b⁺ CTL) prepared by the method of the present invention (Expansion Culture 2) and the parental CTL clone (H25-4) were analyzed for their proliferation. As a result, as shown in FIG. 15, a proliferation-promoting effect was found when expansion culture was carried out after adding one or more of IL-21, IL-12, IL-18, and TL1A in addition to the basal cytokines IL-7 and IL-15.

Further, a proliferation-promoting effect was found also for the parental CTL clone when expansion culture was carried out after adding IL-21, IL-12, IL-18, and/or TL1A in addition to the basal cytokines IL-7+IL-15.

Figure 16:
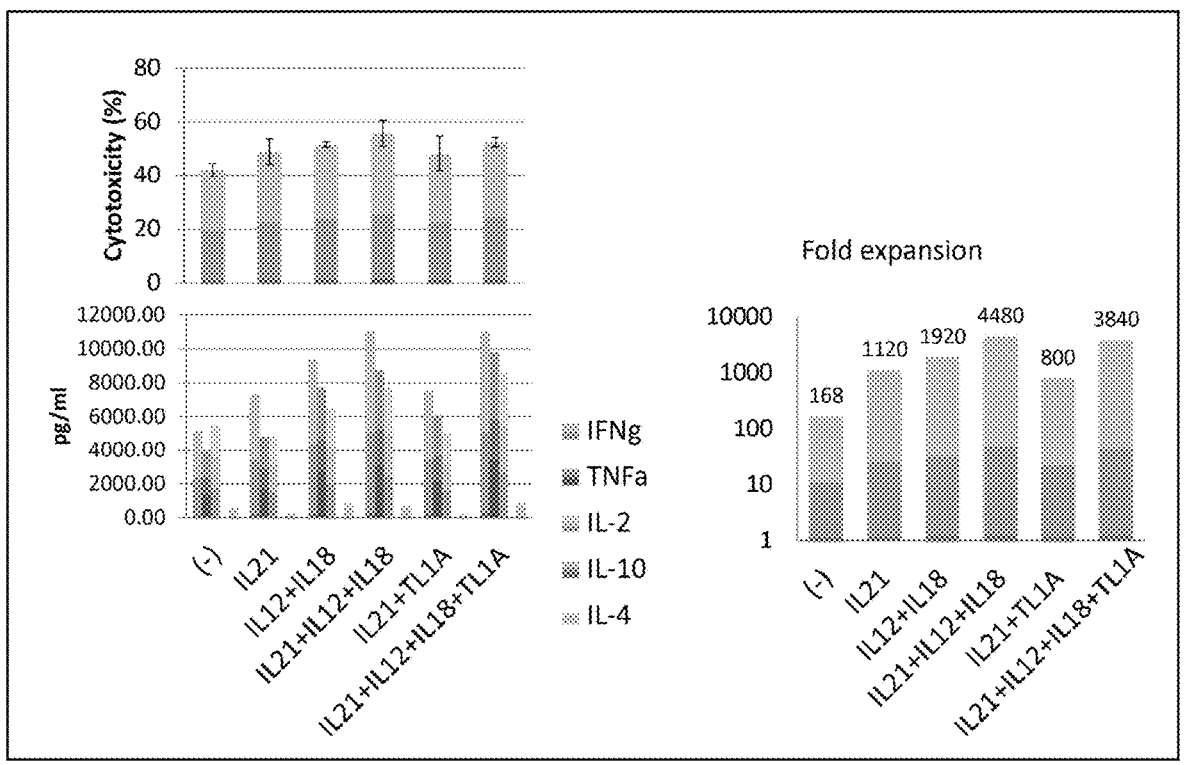
FIG. 16 shows results of measurement of the cytotoxic activity, the cytokine production, and the fold expansion of modified iPSC-CTLs (Modified CD8b+ CTL) in 2-week expansion culture in media containing cytokines.

14. Analysis of Cytokine Production and Cytotoxic Activity Under Antigen Stimulation The modified iPSC-CTLs (Modified CD8b⁺ CTL) prepared by the method of the present invention (Expansion Culture 2) were stimulated with PHA+PBMC, and their cytokine production and cytotoxic activity were investigated. As a result, as shown in FIG. 16, it was found that not only the fold expansion, but also the cytokine productivity and the cytotoxic activity can be increased when expansion culture is carried out after adding one or more of IL-21, IL-12, IL-18, and TL1A in addition to the basal cytokines IL-7 and IL-15.

What is claimed is:

1. A method of producing CD8α⁺β⁺ cytotoxic T lymphocytes, the method comprising:
    (a) culturing CD4/CD8 double-positive T cells in the presence of IL (interleukin)-7 and a T-cell receptor activator, wherein the T-cell receptor activator is an anti-CD3 antibody, thereby producing CD8α⁺β⁺ cytotoxic T lymphocytes, and
    (b) culturing the cells obtained in step (a) in the presence of IL-7, but in the absence of a T-cell receptor activator, wherein the culture (b) is carried out using a culture vessel containing a fibronectin fragment and/or a Notch ligand.

2. The method according to claim 1, wherein the medium further contains IL-21 and Flt3L (Flt3 ligand).

3. The method according to claim 1, wherein the fibronectin fragment is RetroNectin, and the Notch ligand is Delta-like 4 (DLL4).

4. The method according to claim 1, further comprising the following step (c):
    (c) culturing the cells obtained in step (b) in a medium containing IL-7, IL-21, and Flt3L using a culture vessel containing neither a fibronectin fragment nor a Notch ligand.

5. The method according to claim 4, comprising the following steps (a1), (b1), and (c1):
    (a1) culturing CD4/CD8 double-positive T cells in a medium containing IL-7, Flt3L, IL-21, and an anti-CD3 antibody;
    (b1) culturing the cells obtained in step (a1) in a medium containing IL-7, Flt3L, and IL-21, but not containing an anti-CD3 antibody, using a culture vessel containing a fibronectin fragment; and
    (c1) culturing the cells obtained in step (b I) in a medium containing IL-7, IL-21, and Flt3L using a culture vessel containing neither a fibronectin fragment nor a Notch ligand.

6. The method according to claim 4, comprising the following steps (a2), (b2), and (c2):
    (a2) culturing CD4/CD8 double-positive T cells in a medium containing IL-7, Flt3L, and an anti-CD3 antibody;
    (b2) culturing the cells obtained in step (a2) in a medium containing IL-7 and Flt3L, but not containing an anti-CD3 antibody, using a culture vessel containing a fibronectin fragment and a Notch ligand; and
    (c2) culturing the cells obtained in step (b2) in a medium containing IL-7, IL-21, and Flt3L using a culture vessel containing neither a fibronectin fragment nor a Notch ligand.

7. The method according to claim 1, wherein the culture is carried out without using feeder cells.

8. The method according to claim 1, further comprising the step of sorting the CD8$\alpha^+\beta^+$ cytotoxic T lymphocytes obtained.

9. The method according to claim 8, wherein the sorting step is carried out using as an index/indexes, wherein the index/indexes is one or more of CD8$\alpha^+\beta^+$ positivity, CD5 positivity, CD336 negativity, and CD1 a negativity.

10. The method according to claim 1, further comprising the step of performing expansion culture of CD8$\alpha^+\beta^+$ cytotoxic T lymphocytes in a medium containing IL-7, IL-15, and IL-21.

11. The method according to claim 1, further comprising the step of performing expansion culture of CD8$\alpha^+\beta^+$ cytotoxic T lymphocytes in a medium containing IL-7 and IL-15, and one or more of IL-21, IL-18, IL-12, and TL1A.

12. The method according to claim 1, wherein the CD4/CD8 double-positive T cells are induced from pluripotent stem cells.

13. The method according to claim 12, wherein the pluripotent stem cells are induced pluripotent stem (iPS) cells.

14. The method according to claim 12, wherein the induction of the CD4/CD8 double-positive T cells from the pluripotent stem cells comprises the following steps (a) and (b):
 (a) culturing the pluripotent stem cells in a medium supplemented with vitamin C, to induce hematopoietic progenitor cells; and
 (b) culturing the hematopoietic progenitor cells obtained in step (a) in a medium containing vitamin C, FLT3L, and IL-7, to induce CD4/CD8 double-positive T cells.

15. The method according to claim 1, wherein the CD8$\alpha^+$ $\beta^+$ cytotoxic T lymphocytes produced do not show natural killer (NK) activity.

* * * * *